(12) United States Patent
Veilleux et al.

(10) Patent No.: US 10,709,842 B2
(45) Date of Patent: Jul. 14, 2020

(54) DAMPERS AND METHODS FOR PERFORMING MEASUREMENTS IN AN AUTOINJECTOR

(71) Applicant: California Institute of Technology, Pasadena, CA (US)

(72) Inventors: Jean-Christophe Veilleux, Pasadena, CA (US); Joseph Emmett Shepherd, La Canada Flintridge, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 16/511,589

(22) Filed: Jul. 15, 2019

(65) Prior Publication Data
US 2019/0336687 A1 Nov. 7, 2019

Related U.S. Application Data

(62) Division of application No. 15/649,329, filed on Jul. 13, 2017, now abandoned.
(Continued)

(51) Int. Cl.
*A61M 5/20* (2006.01)
*A61M 5/34* (2006.01)
(Continued)

(52) U.S. Cl.
CPC ...... *A61M 5/2033* (2013.01); *A61M 5/31511* (2013.01); *A61M 5/34* (2013.01);
(Continued)

(58) Field of Classification Search
CPC .. A61M 2005/2086; A61M 2005/3143; A61M 5/2033; A61M 5/31511;
(Continued)

(56) References Cited

U.S. PATENT DOCUMENTS 7,938,802 B2 5/2011 Rudzena et al.
7,955,304 B2 6/2011 Guillermo et al.
(Continued)

FOREIGN PATENT DOCUMENTS

EP 2758102 B1 8/2015
WO 2015171777 A1 11/2015

*Primary Examiner* — Suman K Nath
(74) *Attorney, Agent, or Firm* — KPPB LLP

(57) ABSTRACT

Systems and methods for measuring and damping forces within autoinjectors in accordance with embodiments of the invention are disclosed. In one embodiment of the invention, an injection system comprises a syringe disposed within a housing, the syringe having a first end and a second end; a needle disposed at the second end of the syringe; a plunger disposed at the first end of the syringe and configured to move toward the second end of the syringe; a stopper disposed between the plunger and the second end of the syringe; a first damper disposed between the plunger and the stopper, such that the first damper is capable of damping a first event occurring between the plunger and the stopper; and a second damper disposed at the second end of the syringe, such that the second damper is capable of damping a second event occurring at the second end of the syringe.

11 Claims, 22 Drawing Sheets

Related U.S. Application Data

(60) Provisional application No. 62/361,679, filed on Jul. 13, 2016, provisional application No. 62/362,203, filed on Jul. 14, 2016.

(51) Int. Cl.
*A61M 5/315* (2006.01)
*G01B 21/32* (2006.01)
*G01L 9/00* (2006.01)
*A61M 5/31* (2006.01)

(52) U.S. Cl.
CPC ..... *G01B 21/32* (2013.01); *A61M 2005/2086* (2013.01); *A61M 2005/3143* (2013.01); *A61M 2205/332* (2013.01); *A61M 2205/3306* (2013.01); *A61M 2205/70* (2013.01); *G01L 9/00* (2013.01)

(58) Field of Classification Search
CPC ............ A61M 5/34; A61M 2205/3306; A61M 2205/332; A61M 2205/70; G01B 21/32; G01L 9/00
USPC ................... 73/760, 864.11, 864.13, 864.16; 422/501, 502, 504, 505, 516, 922, 923; 436/180
See application file for complete search history.

(56) References Cited

U.S. PATENT DOCUMENTS

| | | | |
|---|---|---|---|
| 9,408,973 | B2 | 8/2016 | Shang et al. |
| 2009/0124981 | A1 | 5/2009 | Evans et al. |
| 2009/0163867 | A1 | 6/2009 | Marshall et al. |
| 2009/0287237 | A1 | 11/2009 | Nicholls et al. |
| 2010/0010454 | A1 | 1/2010 | Marshall et al. |
| 2010/0063457 | A1 | 3/2010 | Crossman et al. |
| 2010/0174305 | A1 | 7/2010 | Marshall et al. |
| 2010/0249820 | A1 | 9/2010 | Evans et al. |
| 2010/0286620 | A1 | 11/2010 | Edginton et al. |
| 2010/0286622 | A1 | 11/2010 | Liu et al. |
| 2010/0324485 | A1 | 12/2010 | Cowe et al. |
| 2010/0324582 | A1 | 12/2010 | Nicholls et al. |
| 2011/0022070 | A1 | 1/2011 | Nicholls et al. |
| 2011/0077599 | A1 | 3/2011 | Wozencroft et al. |
| 2011/0092905 | A1 | 4/2011 | Cowe et al. |
| 2011/0144530 | A1* | 6/2011 | Felder .................. A61F 2/004 600/561 |
| 2011/0144584 | A1 | 6/2011 | Wozencroft et al. |
| 2011/0166521 | A1 | 7/2011 | Marshall et al. |
| 2011/0172602 | A1 | 7/2011 | Eaton et al. |
| 2011/0196311 | A1 | 8/2011 | Bicknell et al. |
| 2011/0202011 | A1 | 8/2011 | Wozencroft et al. |
| 2011/0202080 | A1 | 8/2011 | Nicholls et al. |
| 2011/0313364 | A1 | 12/2011 | Rolfe et al. |
| 2012/0071835 | A1 | 3/2012 | Marshall et al. |
| 2012/0095408 | A1 | 4/2012 | Eaton et al. |
| 2012/0184900 | A1 | 7/2012 | Marshall et al. |
| 2012/0220954 | A1 | 8/2012 | Cowe et al. |
| 2012/0245497 | A1 | 9/2012 | Nicholls et al. |
| 2012/0296276 | A1 | 11/2012 | Nicholls et al. |
| 2013/0035645 | A1 | 2/2013 | Bicknell et al. |
| 2013/0046249 | A1 | 2/2013 | Cowe et al. |
| 2013/0079725 | A1 | 3/2013 | Shang et al. |
| 2013/0190693 | A1 | 7/2013 | Ekman et al. |
| 2013/0197442 | A1 | 8/2013 | Cowe et al. |
| 2013/0204197 | A1 | 8/2013 | Bicknell et al. |
| 2013/0218128 | A1 | 8/2013 | Cowe et al. |
| 2013/0261557 | A1 | 10/2013 | Evans et al. |
| 2013/0281933 | A1 | 10/2013 | Cowe et al. |
| 2013/0281943 | A1 | 10/2013 | Eaton et al. |
| 2013/0310745 | A1 | 11/2013 | Latham David et al. |
| 2013/0310746 | A1 | 11/2013 | Wozencroft et al. |
| 2013/0310758 | A1 | 11/2013 | Wozencroft et al. |
| 2013/0331785 | A1 | 12/2013 | Wozencroft et al. |
| 2013/0331796 | A1 | 12/2013 | Wozencroft et al. |
| 2013/0338601 | A1 | 12/2013 | Cowe et al. |
| 2013/0345642 | A1 | 12/2013 | Cowe et al. |
| 2014/0046269 | A1 | 2/2014 | Eaton et al. |
| 2014/0121691 | A1 | 5/2014 | Hudson et al. |
| 2014/0121693 | A1 | 5/2014 | Nicholls et al. |
| 2014/0228767 | A1 | 8/2014 | Nicholls et al. |
| 2014/0236076 | A1 | 8/2014 | Marshall et al. |
| 2014/0288506 | A1 | 9/2014 | Mumford et al. |
| 2015/0100029 | A1 | 4/2015 | Reitter et al. |
| 2015/0100031 | A1 | 4/2015 | Cowe |
| 2015/0112262 | A1 | 4/2015 | Wozencroft |
| 2015/0119818 | A1 | 4/2015 | Evans |
| 2015/0209525 | A1 | 7/2015 | Bicknell et al. |
| 2015/0250409 | A1 | 9/2015 | Wozencroft et al. |
| 2015/0265775 | A1 | 9/2015 | Cowe |
| 2015/0273158 | A1 | 10/2015 | Cowe |
| 2015/0302818 | A1 | 10/2015 | Santella et al. |
| 2015/0313513 | A1 | 11/2015 | Evans et al. |
| 2015/0314072 | A1 | 11/2015 | Cowe |
| 2015/0314075 | A1 | 11/2015 | Cowe |
| 2016/0015896 | A1 | 1/2016 | Anderson et al. |
| 2016/0022915 | A1 | 1/2016 | Cowe |
| 2016/0106920 | A1 | 4/2016 | Stefansen |
| 2016/0175528 | A1 | 6/2016 | Nicholls et al. |
| 2016/0175536 | A1 | 6/2016 | Tomaszewski et al. |
| 2016/0186709 | A1* | 6/2016 | Walder ................. F02M 65/003 73/114.51 |
| 2016/0193415 | A1 | 7/2016 | Cowe |
| 2016/0228642 | A1 | 8/2016 | Cowe et al. |
| 2016/0250421 | A1 | 9/2016 | Varde et al. |
| 2016/0279343 | A1 | 9/2016 | Farmer et al. |
| 2016/0303331 | A1 | 10/2016 | Evans et al. |
| 2016/0310673 | A1 | 10/2016 | Farmer et al. |
| 2016/0317072 | A1 | 11/2016 | Calvert et al. |
| 2016/0317752 | A1 | 11/2016 | Cowe et al. |
| 2016/0354553 | A1 | 12/2016 | Anderson et al. |
| 2017/0007765 | A1 | 1/2017 | Cowe et al. |
| 2017/0173269 | A1 | 6/2017 | Wozencroft |
| 2017/0182253 | A1 | 6/2017 | Folk et al. |
| 2017/0209653 | A1 | 7/2017 | Cowe et al. |
| 2017/0232201 | A1 | 8/2017 | Holland et al. |
| 2017/0232205 | A1 | 8/2017 | Cowe et al. |
| 2017/0232208 | A1 | 8/2017 | Evans et al. |
| 2018/0015224 | A1 | 1/2018 | Veilleux et al. |
| 2019/0038210 | A1* | 2/2019 | Peliks .................. A61B 5/4325 |

* cited by examiner

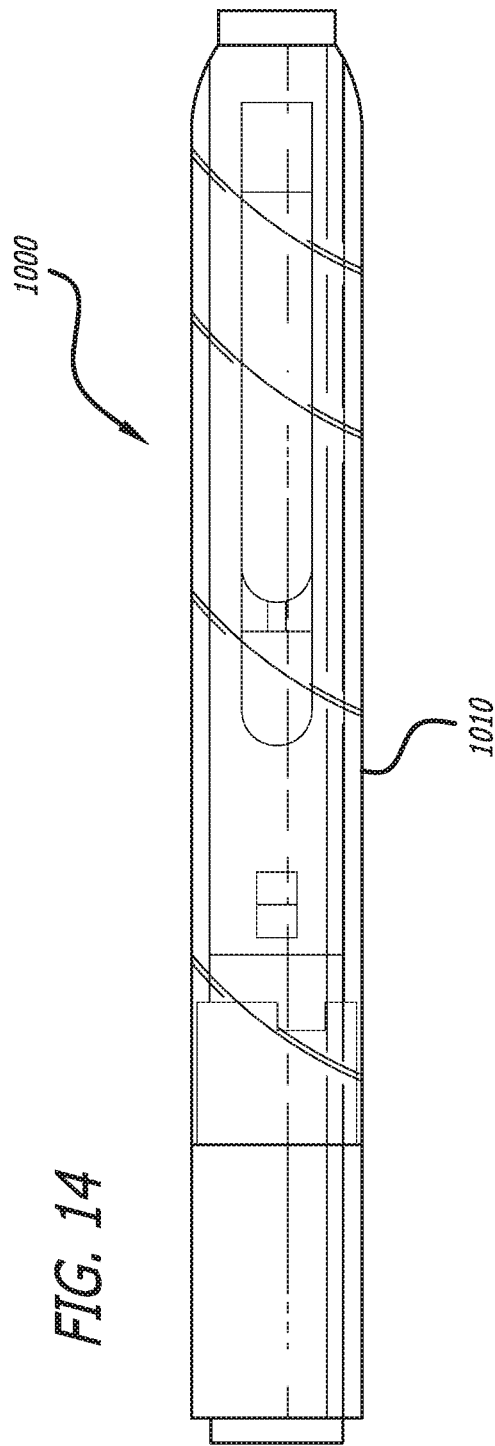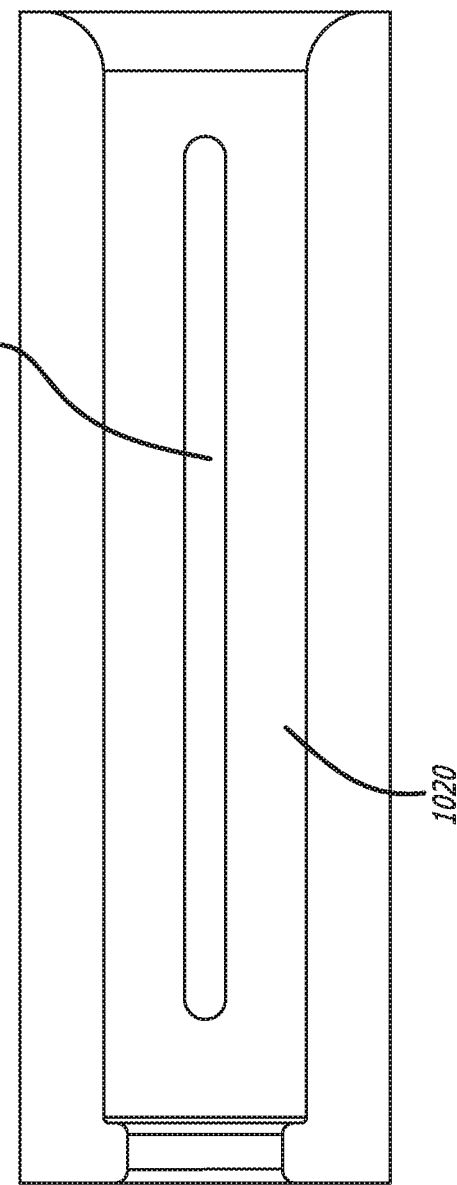

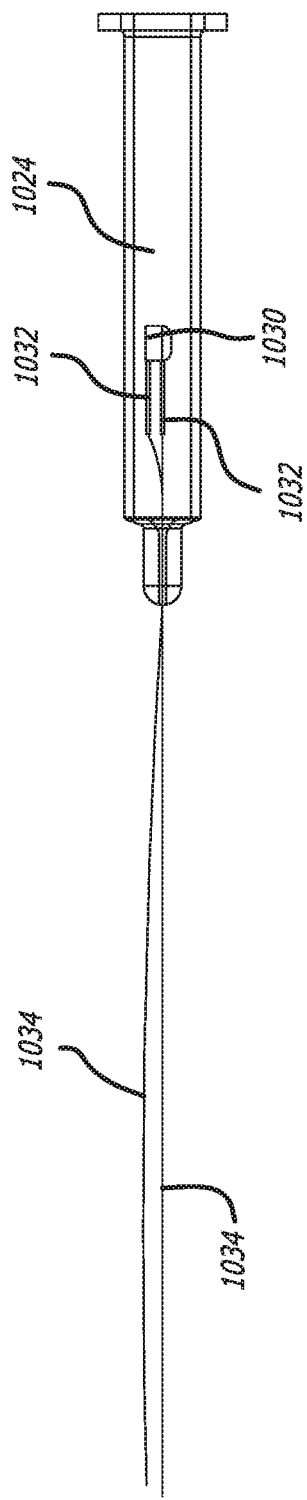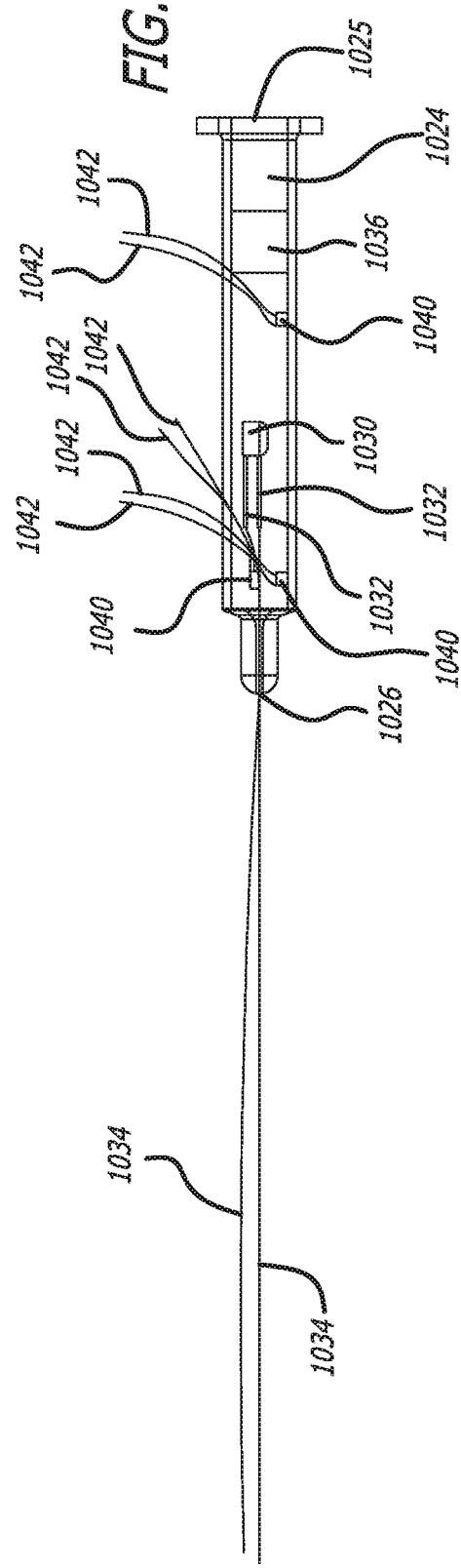

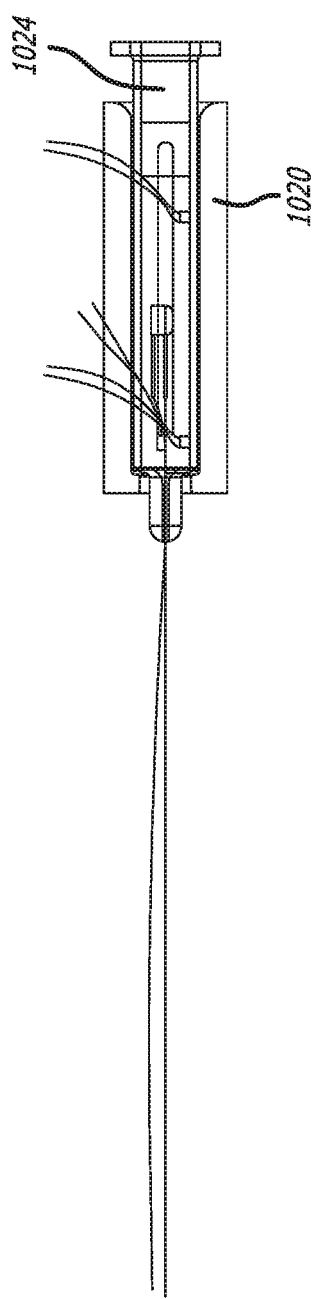
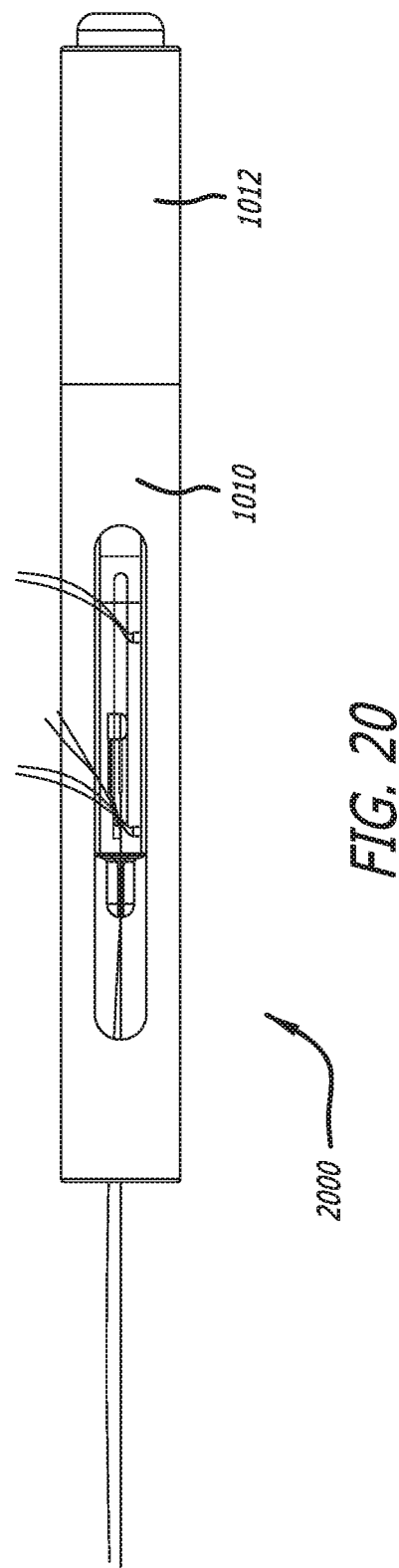

DAMPERS AND METHODS FOR PERFORMING MEASUREMENTS IN AN AUTOINJECTOR

CROSS-REFERENCE TO RELATED APPLICATION(S)

The current application is a divisional of U.S. patent application Ser. No. 15/649,329 entitled "Dampers and Methods for Performing Measurements in an Autoinjector," filed Jul. 13, 2017, which application claims priority to U.S. Provisional Patent Application Ser. No. 62/361,679 entitled "Dampers for Injection Pens," filed Jul. 13, 2016, and U.S. Provisional Patent Application Ser. No. 62/362,203 entitled "In situ Strain and Pressure Measurements in an Injection Pen," filed Jul. 14, 2016, the disclosures of which are herein incorporated by reference in their entirety.

FIELD OF THE INVENTION

This invention generally relates to the damping and measurement of forces in autoinjectors. More particularly, this invention relates to methods for performing in situ strain and pressure measurements in autoinjectors, and damping pressures and strains in autoinjectors.

BACKGROUND

Autoinjectors are commonly used in the pharmaceutical industry. These devices are used both with drugs to be administered in case of emergency (e.g., epinephrine), and with drugs to be administered on a more frequent basis (e.g., alprostadil, exenatide, and etanercept). Autoinjectors are generally considered to be compact and easy to use, and these fully-automated devices can greatly simplify the administration of drugs which cannot be administered orally.

Although the specific design of each autoinjector may differ, many of the devices employ spring-actuated mechanisms. By pressing a button, a syringe needle is inserted into the patient and the drug is delivered. A syringe within the autoinjector may include a plunger fitted within a cylindrical tube or barrel, along which the plunger may slide to expel liquid. Many autoinjectors contain glass syringes.

SUMMARY OF THE INVENTION

Dampers to efficiently dampen peak pressures and strains in the syringes of autoinjectors, and methods to measure such pressures and strains, in accordance with various embodiments of the invention are disclosed.

In one embodiment of the invention, an injection system comprises a syringe disposed within a housing, the syringe having a first end and a second end, wherein the second end comprises an exit opening; a needle disposed at the second end of the syringe; a plunger disposed at the first end of the syringe and configured to move along an interior cavity of the syringe toward the second end of the syringe; a stopper disposed between the plunger and the second end of the syringe, within the interior cavity of the syringe; a first damper disposed between the plunger and the stopper, such that the first damper is capable of damping a first event occurring between the plunger and the stopper; and a second damper disposed at the second end of the syringe, such that the second damper is capable of damping a second event occurring at the second end of the syringe.

In a further embodiment, movement of the plunger is spring-actuated.

In another embodiment, at least one of the first damper or the second damper is formed with viscoelastic foam.

In a yet further embodiment, the first damper is disk shaped.

In another embodiment, the second damper is cylinder shaped.

In yet another embodiment, the first damper is capable of limiting a strain in the syringe during the first event, and the second damper is capable of limiting a strain in the syringe during the second event, such that fracture is prevented in the syringe.

In still another embodiment, the syringe is formed of glass.

In a still further embodiment, the needle receives sufficient force from activation of the plunger to penetrate human skin.

In a yet further embodiment, the needle is fixed to the syringe, and fluid within the interior cavity of the syringe is capable of exiting through the exit opening and a hollow cavity of the needle.

In yet another embodiment, the needle is capable of moving from a retracted position to an advanced position, and fluid within the interior cavity of the syringe is capable of exiting through the exit opening and a hollow cavity of the needle while the needle is in the advanced position.

A method for measuring forces in an injection system, according to another further embodiment of the invention, comprises creating a clear shell with dimensions of an original autoinjector, the clear shell being elongated and hollow for housing components of the original autoinjector, including a syringe and a syringe carrier; installing a pressure transducer inside the syringe; filling the syringe with fluid; installing at least one strain gauge on an outer surface of the syringe; and assembling an instrumented autoinjector. Assembling the instrumented autoinjector may be performed by mounting the syringe with the pressure transducer, the fluid, and the at least one strain gauge into the syringe carrier; and mounting the syringe carrier into the clear shell.

In still another further embodiment, the method further comprises removing a needle from the syringe. Installing the pressure transducer may include inserting at least one magnet wire into the syringe; and connecting a first end of the at least one magnet wire to at least one leadwire of the pressure transducer, wherein a second end of the at least one magnet wire extends out of the syringe through a needle opening of the syringe.

In a still yet further embodiment, the fluid includes deionized water.

In still yet another embodiment, installing the at least one strain gauge includes bonding a portion of at least one leadwire of the at least one strain gauge to the outer surface of the syringe.

In a still further embodiment again, the method further comprises forming an opening in a syringe carrier of the original autoinjector; wherein the at least one strain gauge includes at least one leadwire. Mounting the syringe into the syringe carrier may include directing the at least one leadwire of the at least one strain gauge through the opening formed in the syringe carrier. Mounting the syringe carrier into the clear shell may include directing the at least one leadwire of the at least one strain gauge through an opening of the clear shell.

In still another embodiment again, assembling the instrumented autoinjector is further performed by mounting a power pack of the original autoinjector to the clear shell.

In a yet further embodiment, the method further comprises connecting the at least one leadwire of the pressure transducer and the at least one leadwire of the at least one strain gauge to signal conditioners.

In another further embodiment, the method further comprises mounting the instrumented autoinjector onto a fixture.

In still another embodiment, the method further comprises positioning a high-speed camera to capture movement of components within the instrumented autoinjector upon activation of the instrumented autoinjector.

In still yet another embodiment, the method further comprises activating the instrumented autoinjector; and recording data transmitted from the pressure transducer and the at least one strain gauge.

BRIEF DESCRIPTION OF THE DRAWINGS

FIG. 14 shows an example of an autoinjector with a clear shell in accordance with an embodiment of the invention.

FIG. 15 is a schematic of a syringe carrier with a slit in accordance with an embodiment of the invention.

FIG. 17 shows a schematic of a pressure transducer mounted inside a syringe in accordance with an embodiment of the invention.

FIG. 18 shows a schematic of a syringe instrumented with strain gauges and at least one pressure transducer in accordance with an embodiment of the invention.

FIG. 19 shows a schematic of an instrumented syringe mounted into a syringe carrier in accordance with an embodiment of the invention.

FIG. 20 shows a schematic of a spring-actuated autoinjector instrumented with strain gauges and at least one pressure transducer in accordance with an embodiment of the invention.

DETAILED DESCRIPTION

Figure 1:
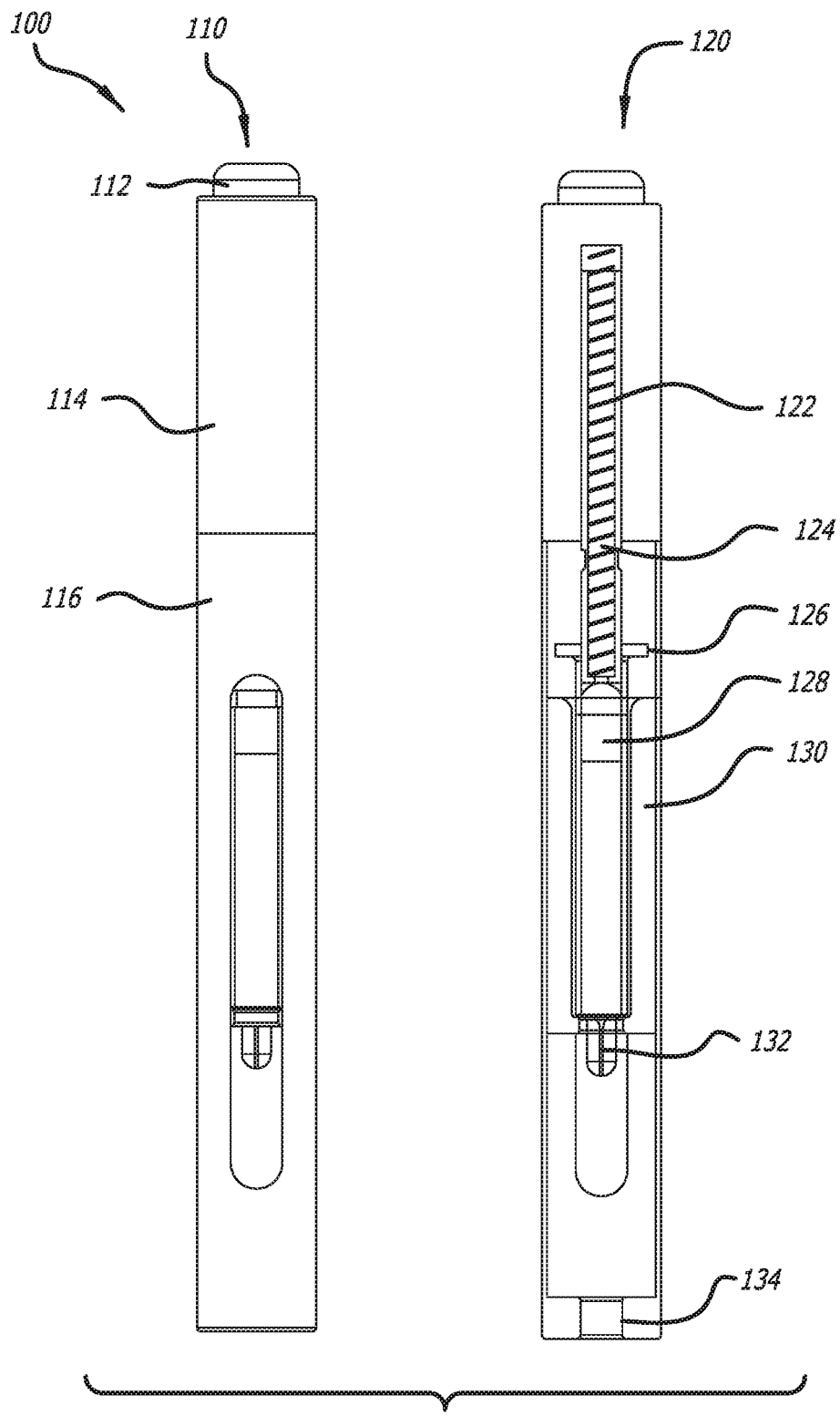
FIG. 1 illustrates certain features of an example of a spring-actuated autoinjector.

Turning now to the drawings, systems and methods for in situ measurement of pressures and strains within autoinjectors, and damping such forces, are illustrated. In many embodiments of the invention, mechanical events exist among the moving components of an autoinjector following its activation, particularly but not limited to when high spring forces are used to, for example, inject viscous drugs. These events may include mechanical impacts, as well as accelerations of components, or other occurrences that may contribute to mechanical failure resulting from fracture of, for example, a glass syringe within the autoinjector.

In several embodiments of the invention, a system and method for performing in situ force measurements within an autoinjector are presented, so as to characterize the stresses and strains to which the components are subjected. Many embodiments of the invention provide for in situ measurements of the pressure inside the syringe and the strains on the outer walls of the syringe, and this may be accomplished using an instrumented autoinjector. The mechanical loads may thus be characterized, potentially allowing for optimization of the design of the autoinjectors, validation of mechanical models, development of insights into device failures, quality control during manufacturing, and certification and/or verification of reliability of devices.

In some embodiments of the invention, the outer shell of an autoinjector is replaced with a transparent replica created using, for example, 3D printing or stereolithography, and high-speed video imaging is used to obtain quantitative data on the motion of the pen components. In certain embodiments of the invention, the syringe is modified by removing the needle, adding a pressure sensor inside, and adding strain gauges on its outer wall. In many embodiments of the invention, the electrical wiring for the sensor and gauges are attached and routed through the device, and a fixture is used to hold the pen in place during testing.

According to a number of embodiments of the invention, dampers are used to damp the mechanical motion of autoinjector components, so as to mitigate events within the device, such as by lowering mechanical impacts and/or reducing abrupt acceleration or deceleration of syringe components. The dampers may be formed using one of various materials, including but not limited to low-resilience, viscoelastic polyurethane foam, various other types of foam, low-density rubber, crushable structures, a frictional damper, and/or a fluidic damper. In certain embodiments of the invention, the dampers include two pieces of foam located in regions of mechanical event occurrences between the components of the autoinjector. According to some embodiments of the invention, the damping system may efficiently damp the deleterious peak pressures and strains in the syringe of an autoinjector.

The measurement of in situ forces within an autoinjector and damping of such forces may have various scientific, medical, commercial, educational and/or other uses. Although specific examples are discussed above and throughout the present specification, it can be readily appreciated that various embodiments of the invention may be implemented in many different fields, and are not limited to those particular examples discussed herein.

Events and Forces within Autoinjectors

FIG. 1 illustrates some key features of one example of a spring-actuated autoinjector 100, having a structure similar to that commonly used in autoinjector devices, including but not limited to the SureClick autoinjector manufactured by the SHL Group of Taoyuan City, Taiwan and used by Amgen of Thousand Oaks, Calif. FIG. 1A shows an exterior view 110 of the autoinjector 100, including power pack activation button 112, power pack 114, and shell 116. FIG. 1B shows the interior 120 of the autoinjector 100, including spring 122, plunger 124, syringe 126, stopper 128 and carrier 130. In this example, the spring 122 is contained within the plunger rod 124. The syringe 126 may be filled with liquid drug solution and mounted inside the carrier 130, which may slide inside the shell 116. This carrier 130 can act as a guide to ensure proper motion of the syringe 126. The syringe needle 132 can exit through end opening 134 to be inserted into the patient's body for delivery of the drug.

In some autoinjectors, the needle 132 may be fixed to the syringe 126, and fluid within the interior cavity of the syringe 126 can exit through the end opening 134 and a hollow cavity of the needle 132. In other autoinjectors, the needle 132 may be capable of moving from a retracted position to an advanced position, and fluid within the interior cavity of the syringe 126 can exit through the end opening 134 and a hollow cavity of the needle 132 while the needle 132 is in the advanced position.

Figure 2:
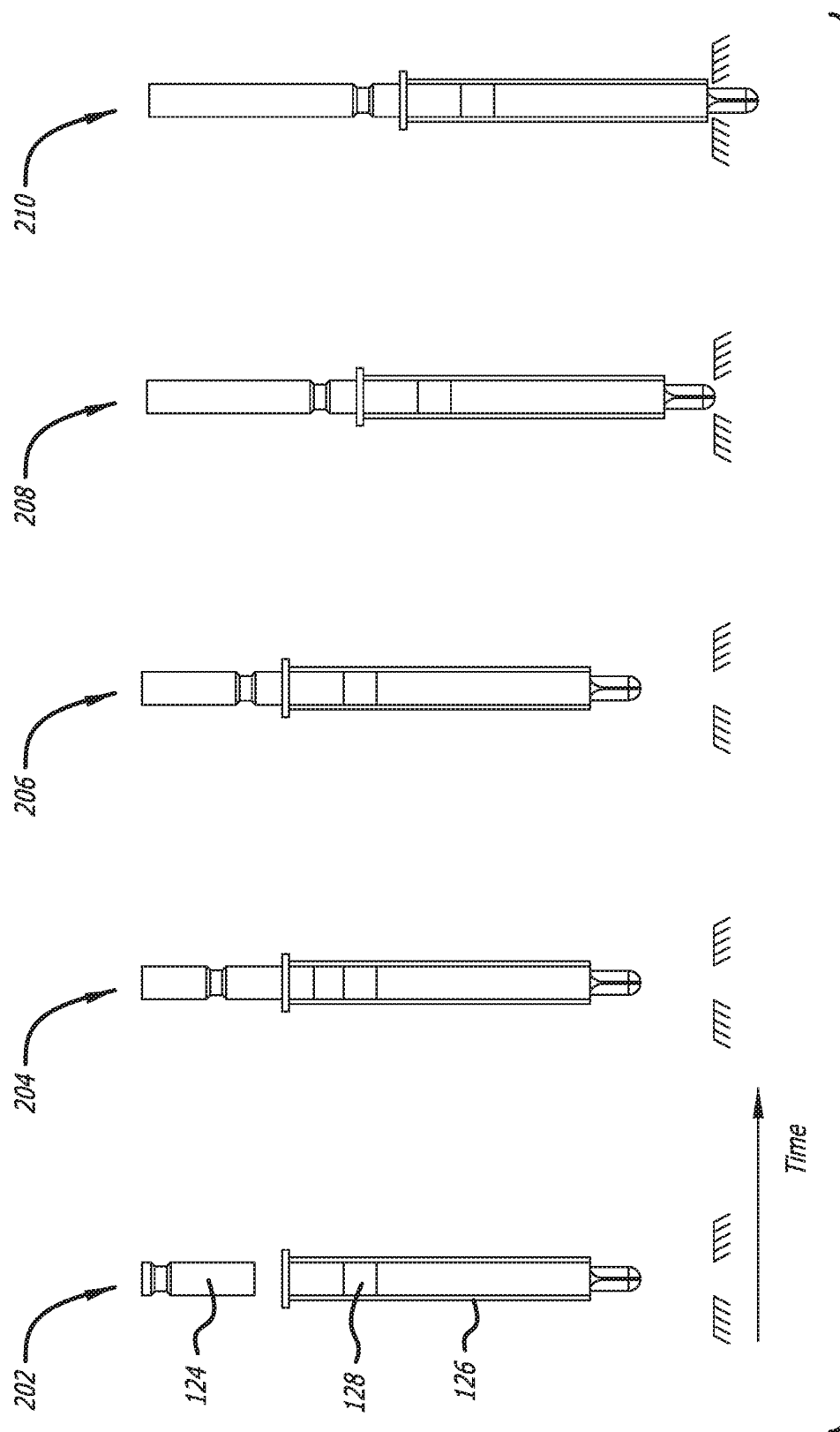
FIG. 2 is a diagram showing selected mechanical events during operation of an autoinjector.

Referring to FIG. 2, when a user activates (202) the autoinjector 100 by depressing the power pack button 112, the internal mechanism of the power pack 114 releases the spring 122. The plunger 124 is then accelerated (204) downward as a result of the spring force and impacts (206) the stopper 128. In some autoinjectors according to other embodiments of the invention, the plunger may be disposed, prior to its downward movement, to be already in contact with the stopper. In such cases, the spring force may nonetheless result in a significant acceleration of the syringe.

We refer herein to such a mechanical occurrence of an impact, high acceleration, and/or other mechanical interaction upon spring activation as the first event 206, and this is when the syringe 126, the carrier 130 and the liquid contained inside the syringe 126 are set into motion. Immediately after the first event, there is a relative motion between the stopper 128 and the syringe 126 which results in the production of a pressure wave below the stopper 128, inside the liquid within the syringe 126. In cases where an air-filled gap is introduced between the liquid and the stopper 128, for example, in the process of filling the syringe with the drug solution, the production of this pressure wave in the fluid may take place simultaneously with the compression of the air gap. The pressure wave will initially travel downward before it reflects off the converging section of the syringe 126 close to the needle 132. This internal pressure can create stress and strain in the syringe 126.

The syringe 126 then continues to accelerate (208) from the spring force. A second event 210 is then observed when the syringe 126 and its carrier 130 reach their travel limit, and both the liquid and the syringe 126 stop moving. This sudden stop of the syringe's motion can be transmitted to the liquid, generating a pressure wave. This pressure originates from the bottom of the syringe 126 (i.e., close to the convergent section) and travels toward the top. This internal pressure can create stress and strain in the syringe 126. The sudden stop of the syringe 126 can also generate elastic (axial) waves propagating along the syringe 126, away from the location of the contact between the syringe 126 and the carrier 130, which can create additional stress and strain in the syringe 126. The stress and strains (hoop and axial) in the syringe 126 that are associated with the second event 210 can be due to the superposition of the axial mechanical loading of the glass as well as the internal pressure in the liquid.

In experimental situations, it may be possible to observe a third event if the syringe 126 and/or carrier 130 rebounds after the second event. However, the strains resulting from this event are typically much lower than the strains associated with the preceding two events. In addition, if the first and second events are properly mitigated through the use of efficient dampers, a significant third event can be avoided. The third event may also potentially be eliminated in clinical situations, as a result of resistance to the syringe motion created by human tissue upon the needle penetrating under the skin.

Figure 4:
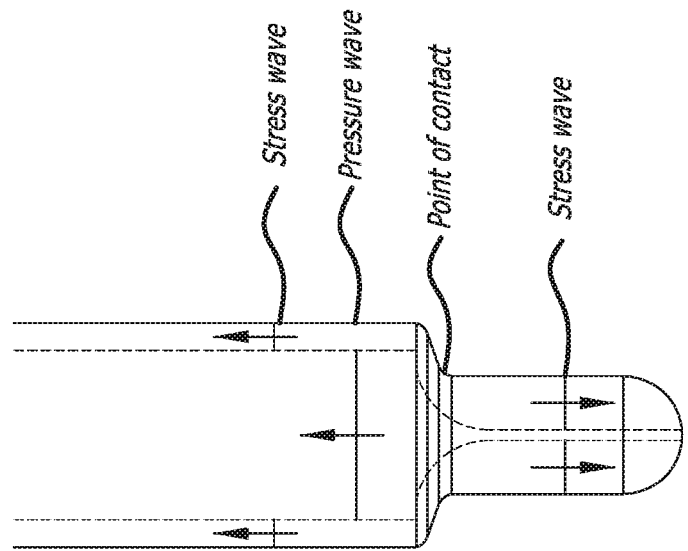
FIG. 4 illustrates example pressure and stress waves produced at a second event in an autoinjector with no air gap, as observed in accordance with an embodiment of the invention.
Figure 3:
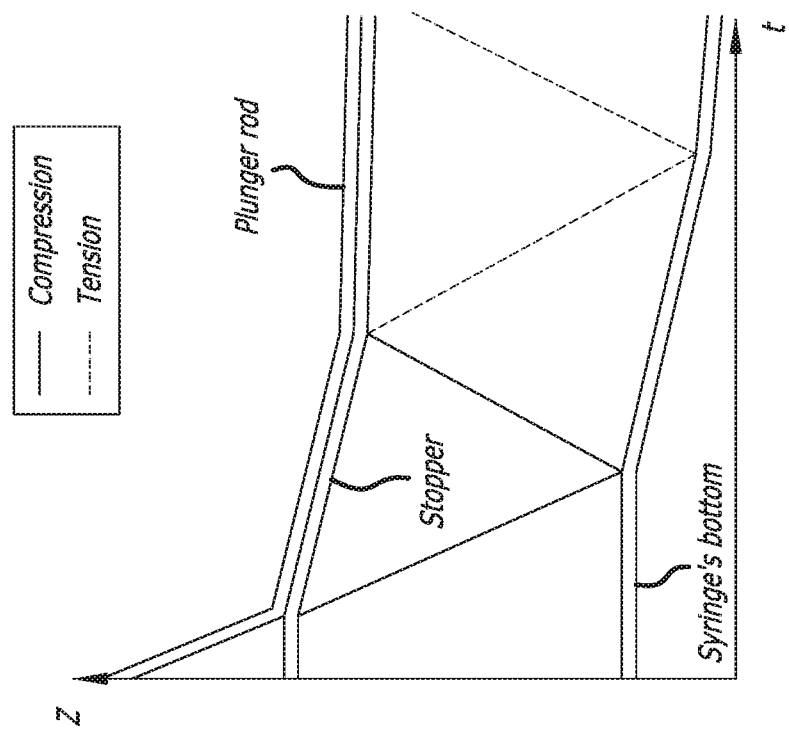
FIG. 3 is a space-time diagram for an example of a first event in an autoinjector with no air gap, as observed in accordance with an embodiment of the invention.
Figure 5:
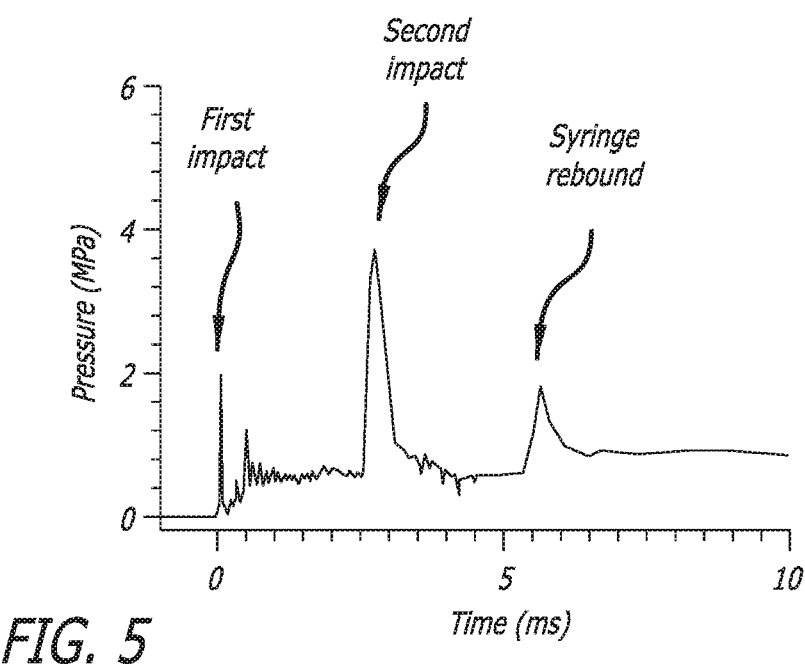
FIG. 5 is a chart illustrating example pressures in liquid above a cone area of a syringe mounted in an autoinjector with no air gap, as measured in accordance with an embodiment of the invention.
Figure 6:
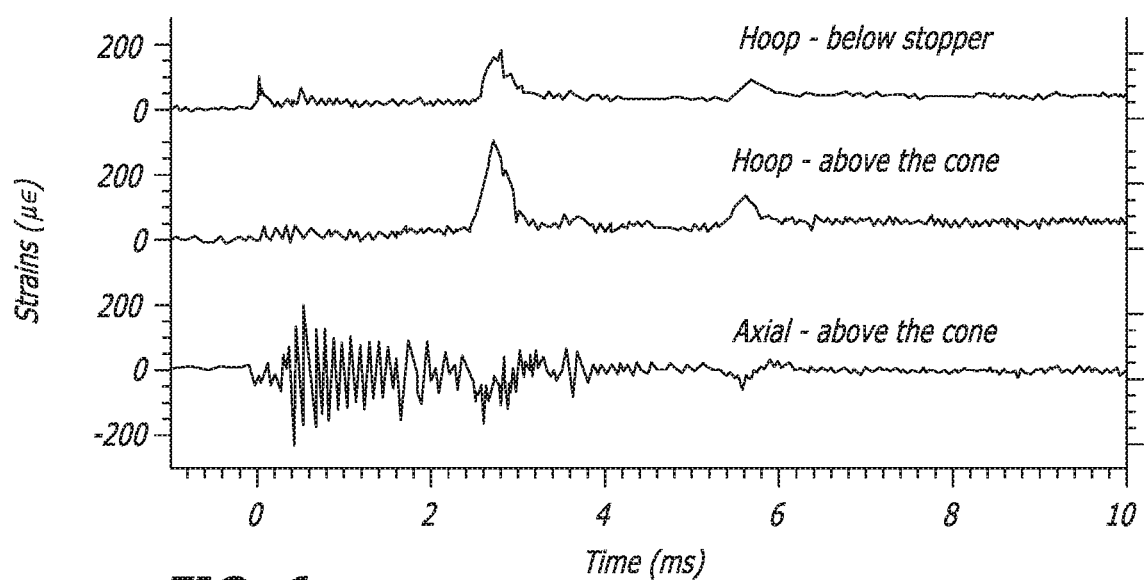
FIG. 6 is a chart illustrating example strains in a glass syringe in an autoinjector with no air gap, as measured in accordance with an embodiment of the invention.

It may be observed in an autoinjector without an air gap between the stopper and the liquid that the first event produces a compression wave in the liquid. This compression wave can initiate the translational motion of the syringe upon reaching its bottom end. The pressure wave can also create stress and strain in the glass syringe. FIG. 3 shows a space-time diagram for one example of this first event. The second event may be observed to produce a compressive stress wave in the barrel of the syringe and a tensile stress wave in the tip of the syringe. The abrupt deceleration of the liquid can also produce a compression wave in the liquid. FIG. 4 illustrates pressure and stress waves produced at one example of the second event. FIG. 5 illustrates example pressures in the liquid above the cone area, and FIG. 6 illustrates example strains in the glass syringe, for an autoinjector without an air gap.

Figure 7:
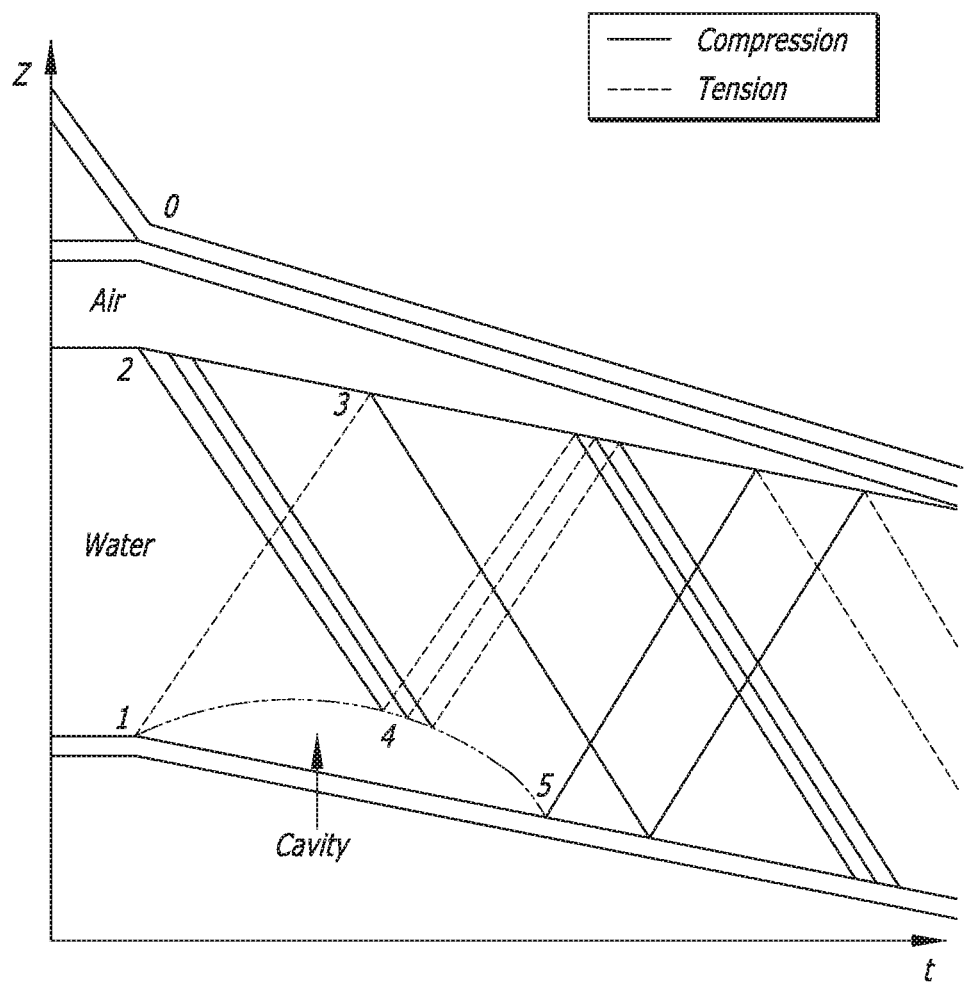
FIG. 7 is a space-time diagram for an example of a first event in an autoinjector with an air gap, as observed in accordance with an embodiment of the invention.
Figure 8:
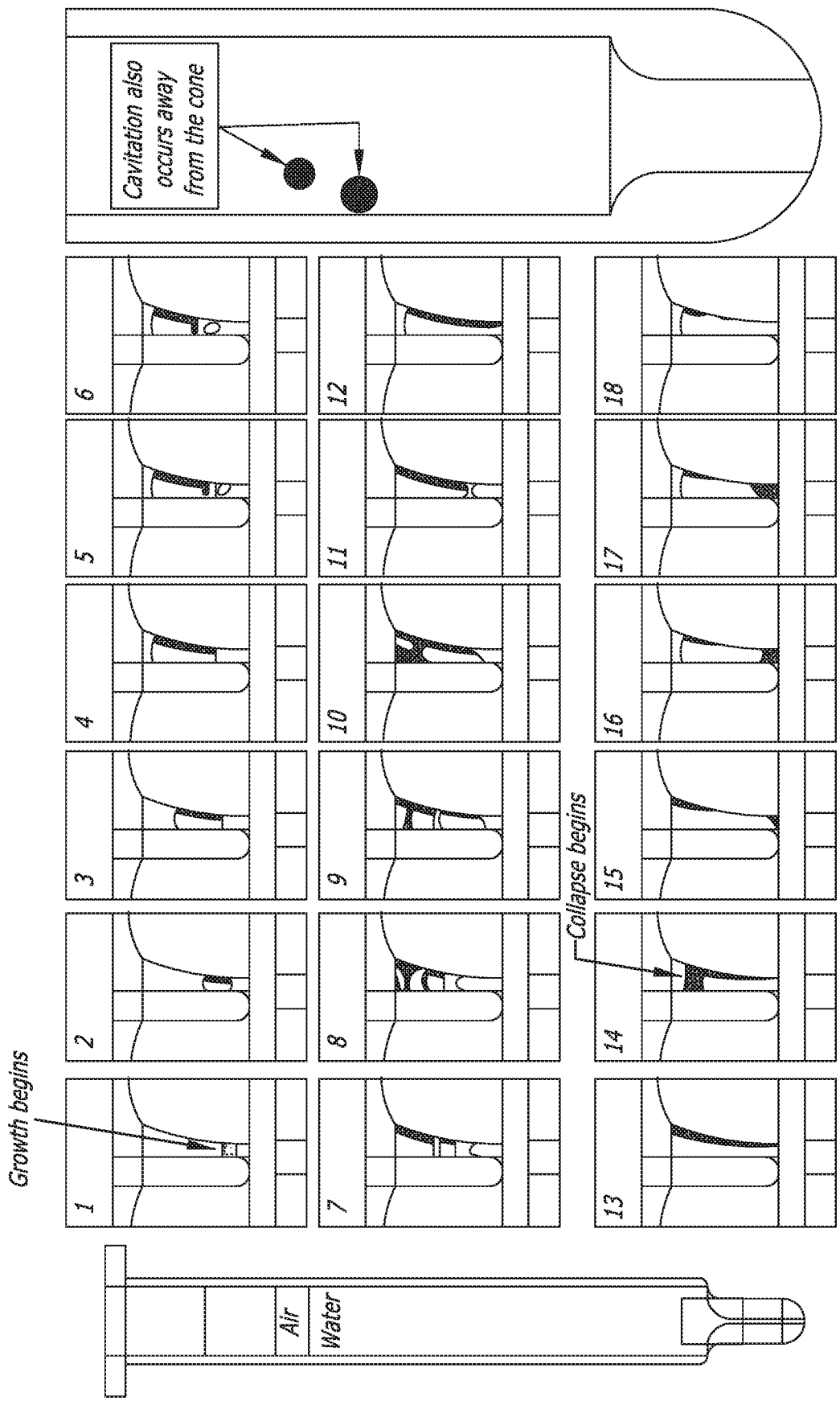
FIG. 8 illustrates an example of growth and collapse of a cavity in the cone area at the first event, and an example of cavitation outside the cone, in an autoinjector with an air gap, as observed in accordance with an embodiment of the invention.
Figure 9:
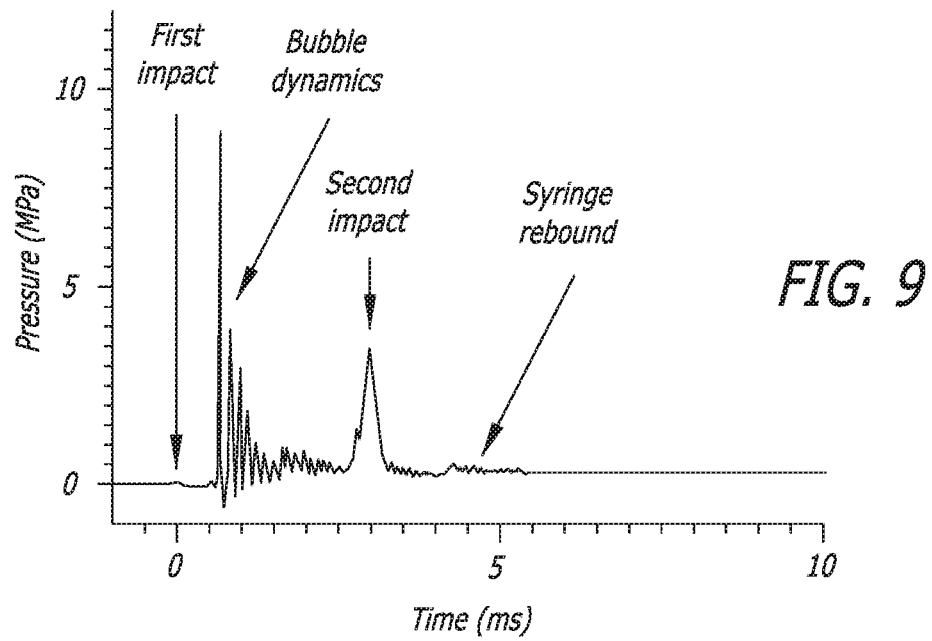
FIG. 9 is a chart illustrating example pressures in liquid above a cone area in an autoinjector with an air gap, as measured in accordance with an embodiment of the invention.
Figure 10:
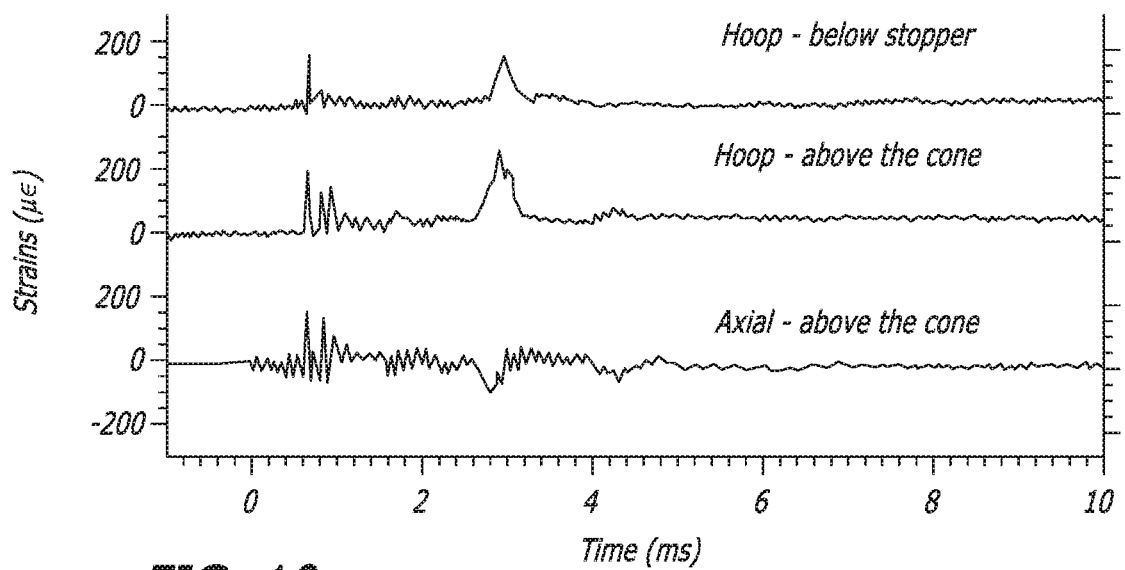
FIG. 10 is a chart illustrating example strains in a glass syringe in an autoinjector with an air gap, as measured in accordance with an embodiment of the invention.

In an autoinjector with an air gap between the stopper and the liquid, it may be observed that this air gap significantly changes the wave dynamics at the first event. FIG. 7 illustrates a space-time diagram for an example of a first event in an autoinjector with an air gap, with events numbered 1-5 in the diagram. Event 0 indicates the occurrence of a first event at which, in this case, the plunger impacts the stopper. At Event 1, the relative motion between the stopper and the syringe is substantial. The frictional force accelerates the syringe downward and this creates tension in the cone area resulting into cavitation. At Event 2, the slow, isentropic compression of the air gap pressurizes the syringe. At Event 3, the tension wave produced in the cone reflects at the air-water interface and can become a compression wave. At Event 4, the pressure increase in the syringe due to the compression of the air gap can cause the cavity in the cone to stop growing and to collapse. At Event 5, the violent collapse of the cavity produces shock waves. FIG. 8 shows the growth and collapse of a cavity in the cone area at the first event and evidence of cavitation outside the cone, with frames separated by 30 µs. FIG. 9 illustrates example pressures in the liquid above the cone area, and FIG. 10 illustrates example strains in the glass syringe, for an autoinjector with an air gap.

Thus, the relative timing of the syringe's acceleration and the pressurization of the syringe can be significant. When there is no air gap, pressurization and acceleration of the syringe may occur almost simultaneously. In such situations, the pressures and strains that occur may result in mechanical failure of the syringe, in especially but not limited to the conical section of the syringe where sharp pressure waves can be amplified. When there is an air gap, the pressurization of the syringe may be delayed. The latter situation can result in transient cavitation and produce shock waves which, in turn, may further cause failure of the syringe.

Figure 11:
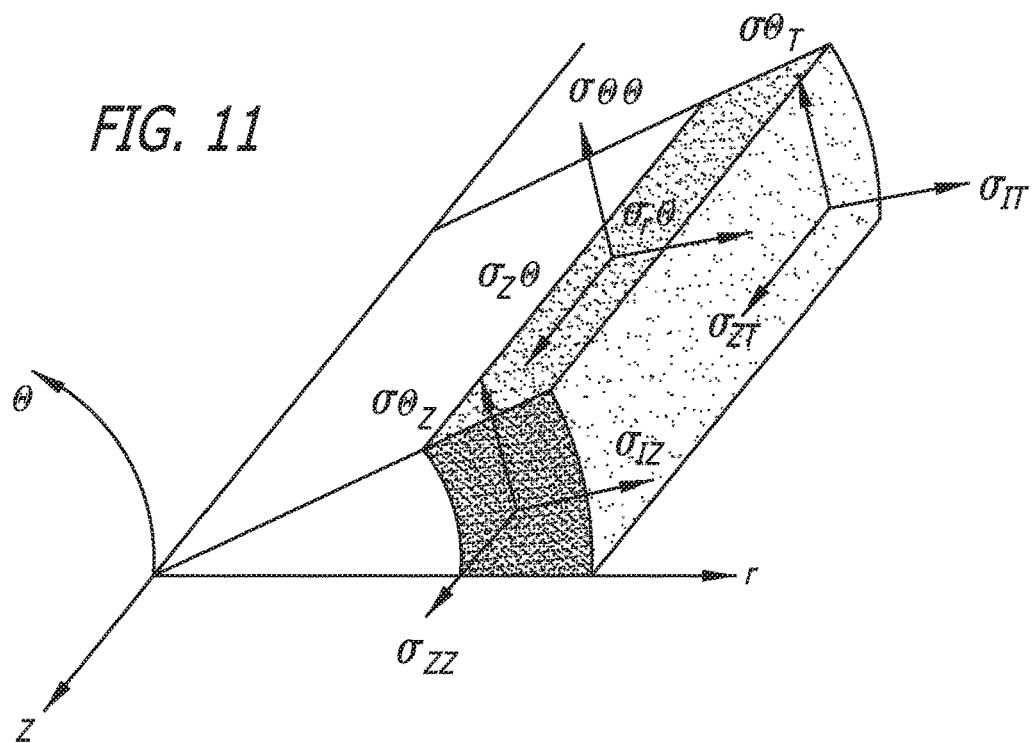
FIG. 11 is a conceptual diagram showing an example of axial, radial and hoop stress.
Figure 12:
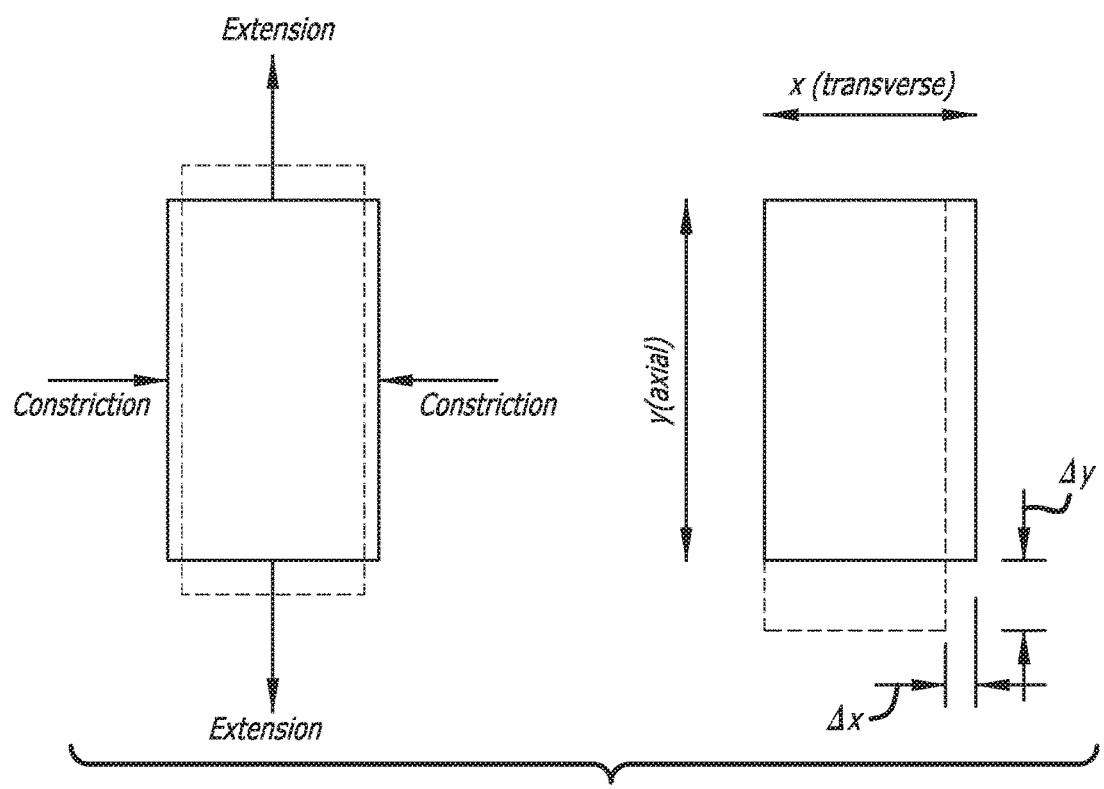
FIG. 12 is a conceptual diagram showing an example of strain produced by stress.

Stress, like pressure, is a force per unit area. Stresses can be observed in various directions with respect to an object. For example, in the diagram of FIG. 11, axial stress $\sigma_{zz}$ may act along the z-axis on a plane perpendicular to the z-axis; radial stress $\sigma_{rr}$ may act along the r-axis on a plane perpendicular to the r-axis; and hoop stress $\sigma_{\theta\theta}$ may act along the θ-axis on a plane perpendicular to the θ-axis. A strain may indicate the response of a system to an applied stress. Engineering strain may be defined as an amount of deformation as a result of an applied force, divided by the initial length of the material. Thus, stresses can produce strains. As an example, in FIG. 12, a stress is applied in the y-direction. This stress produces both a deformation Δy along the y-axis, as well as a deformation Δx along the x-axis due to the Poisson effect, in which materials tend to expand perpendicularly to a direction of compression.

According to certain embodiments of the invention, methods for measuring forces within autoinjectors have indicated that the stress and strains associated with the first and second events can be substantial. Thus, there is a potential for causing mechanical failure such as but not limited to fracture of the syringe that is formed of, for example, glass. This may particularly be an issue when high spring forces are used to inject viscous drugs.

The high stresses and strains experienced in the activation of an autoinjector may be associated with transient forces that are a consequence of the rapid acceleration and deceleration of the syringe. These transient loads are typically not necessary for the operation of the device, but rather a consequence of the lack of damping in the mechanical operation of the standard autoinjectors. In many embodiments of the invention, damping of the mechanical motion is used to eliminate the deleterious peak strains and pressure while maintaining the injection function of the device.

While events and forces within autoinjectors used for medication delivery are described above with respect to FIGS. 1 to 12, the concepts may be applicable to various other systems utilizing spring-activated mechanisms and/or syringe devices. Methods and systems for in situ measurement of stresses and strains in autoinjectors in accordance with a number of embodiments of the invention are discussed further below.

In Situ Strain and Pressure Measurements in an Autoinjector

According to certain embodiments of the invention, methods and systems for measuring the liquid pressure and strains in an autoinjector upon actuation of the device may provide understanding regarding some failure modes of autoinjectors and/or confirmation of manufacturing quality. In many embodiments of the invention, an autoinjector sample is instrumented for pressure and strain measurements. A pressure sensor, such as but not limited to a piezoelectric pressure transducer, may be installed inside the syringe. It may be connected using magnet wires routed through the hole for the needle. The magnet wires may be formed of copper or aluminum wire coated with a thin layer of insulation. Multiple strain gauges may be installed on the outer wall of the syringe. The strain gauges may be connected using magnet wires routed through a slit in the syringe carrier. In some embodiments of the invention, high-speed digital video cameras are used to visualize the plunger, the stopper and the syringe upon actuation, as well as to observe any transient cavitation taking place in the syringe.

Figure 13:
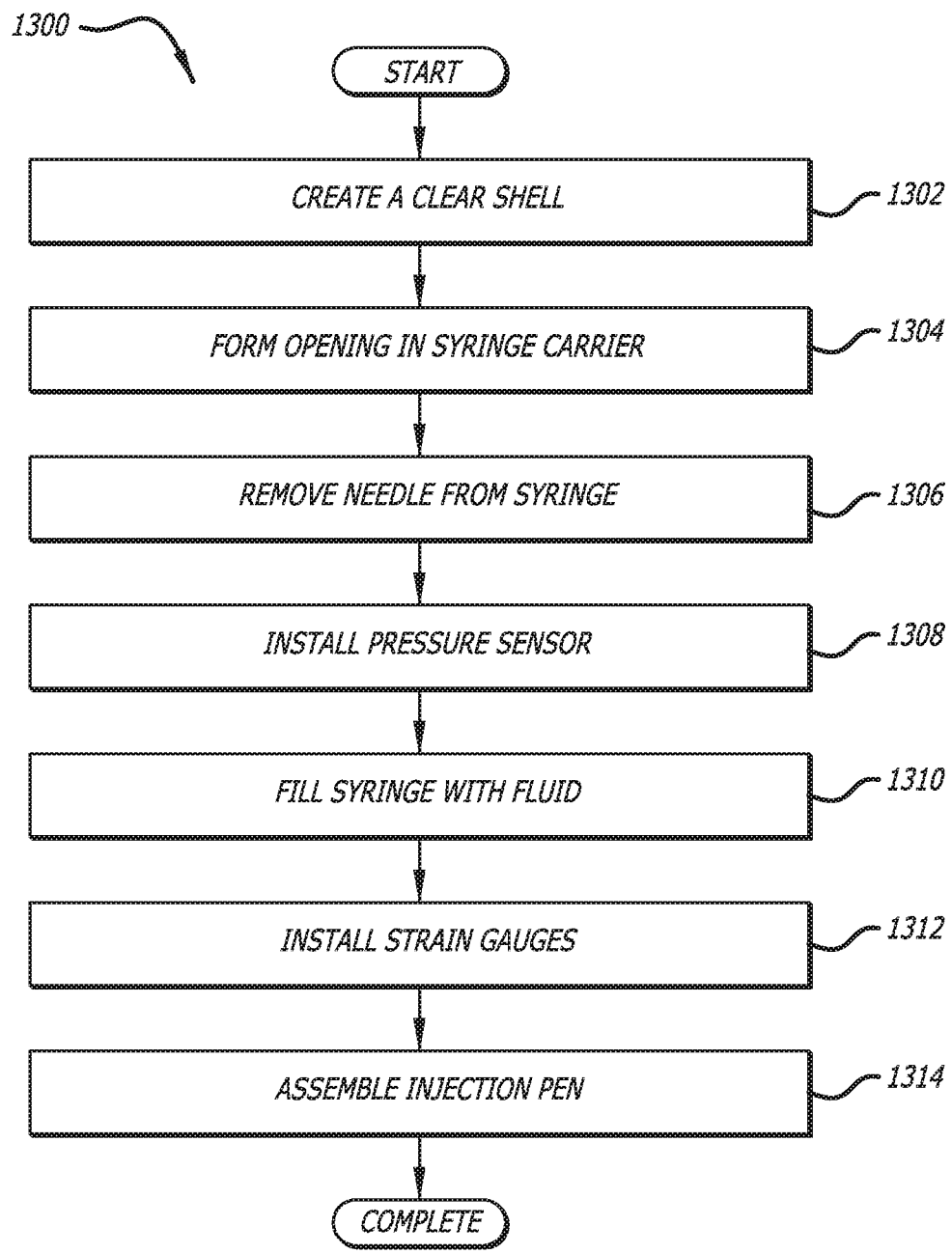
FIG. 13 is a flow chart illustrating a method for instrumenting an autoinjector in accordance with an embodiment of the invention.

Referring to FIG. 13, in a number of embodiments of the invention, a method 1300 for instrumenting an autoinjector for force measurements includes creating (1302) a clear shell, so as to allow for imaging of the moving components. The imaging may provide the ability to verify the sequence of events and timing within the device. Quantitative image analysis can enable measurements of the velocities of various components in time, the impact velocity between the various components, and the accelerations of various components. The clear shell may be fabricated by one of various methods of manufacture, including but not limited to three-dimensional (3D) printing such as by 3D Systems of Rock Hill, S.C. An example of an autoinjector 1000 with a clear shell 1010 is shown in FIG. 14. The clear shell 1010 may be formed to be completely clear, or partially clear so as to expose particular components within the autoinjector.

In many embodiments of the invention, an opening is formed (1304) in the syringe carrier. The opening can allow leadwires of strain gauges mounted, for example, on the outer wall of the syringe, to exit and be connected to a signal conditioner or bridge. The opening can be formed in one of various shapes, including but not limited to that of an oblong slit, rectangle, circle, or any formation allowing the exit of the relevant wires. In addition, multiple openings or other configurations may be used to allow for the exit of the gauge wires. An example of syringe carrier 1020 with an oblong slit 1022 for the leadwires is shown in FIG. 15.

According to several embodiments of the invention, the needle in the syringe is removed (1306) to allow pressure sensor wires to run through the bottom opening of the syringe, from which the needle exits the syringe. Various methods may be used to remove the needle. One manner of removing the needle entails heating the tip of the syringe using, for example, a blow torch or another suitable heat source. The needle may then be pulled out of the syringe using, for example, pliers or any suitable tool. Alternatively, a new syringe may be fabricated without a needle.

Figure 16:
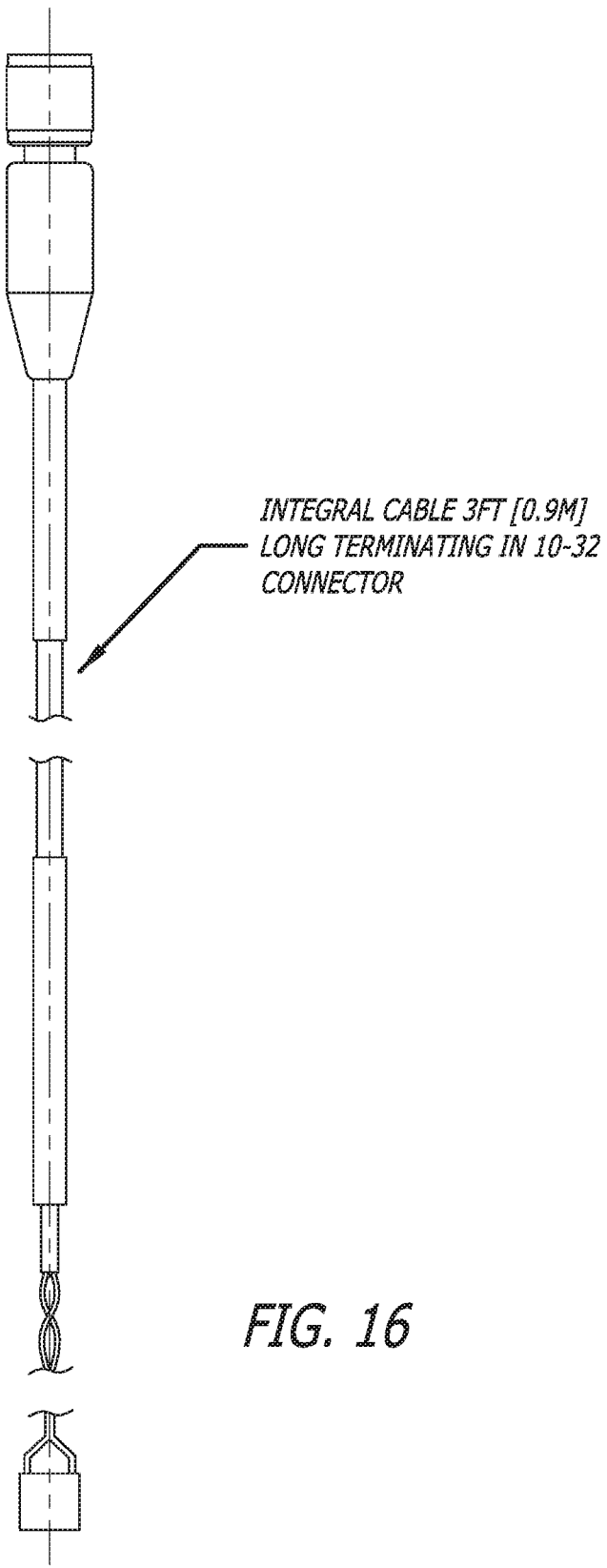
FIG. 16 is a schematic for a PCB 138M186 tourmaline underwater blast pressure sensor.

To measure the liquid pressure during functioning of the autoinjector, a pressure transducer is installed (1308) in many embodiments of the invention. One of various pressure transducers may be used, including but not limited to a PCB 138M186 tourmaline underwater blast pressure sensor from PCB Piezotronics of Depew, N.Y., a schematic for which is shown in FIG. 16.

In a number of embodiments of the invention, the leadwires of the pressure transducer are cut to a short length, for example, such that there are 1.0 to 1.5 inches of leadwires connected to the pressure transducer. Two magnet wires may be introduced inside the syringe from the bottom opening of the syringe. In certain embodiments of the invention, the magnet wires may be cut short so as to minimize noise capture, while maintaining a workable length for purposes of installing the pressure transducer. The length of the magnet wires may be 6 to 12 inches in certain embodiments of the invention. The gauge of the magnet wires may be chosen according to the diameter of the bottom opening, which can differ from one syringe to the other. As an example, American wire gauge (AWG) 34 or 38 may potentially be used with a syringe of an autoinjector similar to the device shown in FIG. 1. Any insulating coating of the wires may be removed at both ends of each magnet wire over a distance of, for example, approximately one quarter of an inch. This can be done using various tools, including but not limited to a razor blade, a solvent and/or heat. The magnet wires may then be connected to the pressure transducer using, for example, a soldering iron and rosin-core solder.

In several embodiments of the invention, a thin coating of insulating material may be applied on the connections. The insulating material can include one of various types of coatings, including but not limited to liquid polyurethane coating typically used to protect strain gauges such as the M-Coat A from Micro-Measurements/VPA of Wendell, N.C., as well as non-conductive epoxy. This protective coating may protect the pressure gauge from being shorted should the two connections come into contact during experimentation. Additionally or alternatively, the pressure gauge may be positioned so as to prevent contact between the two connections.

The pressure gauge may be positioned within the syringe by, for example, pulling on the magnet wires outside the syringe. In many embodiments of the invention, the pressure transducer is positioned to float in syringe liquid, enabling a straightforward interpretation of the liquid pressure measurement. FIG. 17 shows a simplified schematic of a pressure transducer 1030 mounted inside a syringe 1024 according to an embodiment of the invention. The leadwires 1032 of the pressure sensor 1030 are connected to magnet wires 1034 running through the opening at the bottom of the syringe 1024.

In many embodiments of the invention, the syringe is filled (1310) using deionized water. Using normal water poses a higher risk of shorting the pressure transducer, which may impair the measurements. The syringe may also be filled with a drug solution. Once the fluid is inside the syringe, a stopper (or piston) 1036 can be introduced from the top 1025 of the syringe 1024, as shown in FIG. 18. In a number of embodiments of the invention, the bottom opening 1026 of the syringe 1024 is sealed using one of various materials including but not limited to 5-minute epoxy. The sealant may prevent the magnet wires 1034 from moving and fix the position of the pressure transducer 1030 inside the syringe 1024. The sealant may prevent the stopper 1036 from being pushed further down into the syringe 1024 when performing the experiment, which could damage the pressure transducer 1030.

As shown in FIG. 18, strain gauges 1040 may be installed (1312), according to many embodiments of the invention, on the outer surface of the syringe 1024. The strain gauges 1040 may be placed at various locations along the barrel of the syringe 1024, and the locations may be modified depending on the measurement requirements of a particular experiment. In certain embodiments of the invention, the strain gauges 1040 may be placed away from areas where the first and second events occur, so as to avoid erroneous measurements resulting from direct impact by the device components to the strain gauges. As an example, a strain gauge may be placed close to the converging section of the syringe to monitor transient cavitation that could take place in the vicinity of the cone. Alternatively, strain gauges could be placed on other components of the autoinjector which are subjected to large stresses and strains.

In accordance with certain embodiments of the invention, to improve the adherence of the strain gauges to the surface of the syringe 1024, local abrasion of the syringe surface may be performed where the gauges will be mounted. On a glass syringe, this can be performed using one of various tools, including but not limited to a rotary tool with an aluminum oxide grinding stone. Following this, the outer wall of the syringe may be cleaned, conditioned and neutralized. This can be achieved, for example, using various substances such as but not limited to the CSM-2 degreaser, the MCM-1-A conditioner and the MN5A-1-M neutralizer from Micro-Measurements/VPA of Wendell, N.C.

Various types of strain gauges may be used, including but not limited to miniature strain gauges such as the C2A-06-015LW-120 from Micro-Measurements/VPA of Wendell, N.C. The leadwires 1042 of the strain gauges 1040 may be cut so as to end, for example, approximately 2 inches away from each strain gauge 1040. Any insulating coating may be removed from the tips of the leadwires 1042. This can be done using various tools such as but not limited to a razor blade or a solvent. Use of heat may damage the strain gauge.

The strain gauges 1040 may be bonded to the outer surface of the syringe. On a glass surface, one of various bonding substances may be used, including but not limited to that from an M-Bond 200 kit from Micro-Measurements/VPA of Wendell, N.C. or any equivalent product. After bonding each gauge, pressure may be applied on the gauge for a period, such as at least 2 minutes, to maximize adherence to the surface. The gauge adherence may then be verified to ensure proper bonding to the surface. This can be done using a variety of methods, such as but not limited to by trying to lift the corners of the strain gauge 1040 using fine tweezers.

In certain embodiments of the invention, a protective coating such as but not limited to a liquid polyurethane coating M-Coat A from Micro-Measurements/VPA of Wendell, N.C., may be applied on the gauges 1040. The leadwires 1042 of the strain gauges 1040 may also be bonded to the surface of the syringe. This can be done using a variety of methods, such as but not limited to applying a small piece of adhesive tape on the leadwires 1042, as closely as possible to the strain gauges 1040. Bonding the leadwires 1042 to the syringe surface may aid in preventing the gauges 1040 from being removed from the syringe surface, should the leadwires 1042 be pulled when being reconnected to a signal conditioner/bridge. FIG. 18 shows a simplified schematic of the instrumented syringe with the strain gauges 1040 installed.

The autoinjector can be assembled (1314) according to many embodiments of the invention. Prior to mounting the syringe 1024 in the carrier 1020, the leadwires 1042 of the strain gauges 1040 may be wrapped around the surface of the syringe 1024. The syringe 1024 can then be mounted into the syringe carrier 1020, and tweezers or any other appropriate tool can be used to pull the leadwires 1042 through the opening 1022. FIG. 19 shows a simplified schematic of the resulting assembly.

The leadwires 1042 of the strain gauges 1040 may then be wrapped around the carrier 1020. The syringe carrier 1020 with the syringe 1024 may be mounted inside the clear shell 1010. The leadwires 1042 of the strain gauges 1040 may again be pulled through a slot of the shell 1010. Finally, the power pack 1012 can be installed, with an example of the resulting instrumented autoinjector 2000 shown in FIG. 20.

The instrumented autoinjector 2000, according to many embodiments of the invention, is version of an actual device being tested with minimal modifications to its components, so as to achieve results as accurate as possible. Specifically, the instrumented autoinjector 2000 may be tested to measure the liquid pressure following actuation of the device, as well as the hoop and axial strains on the outer wall of the syringe.

Figure 21:
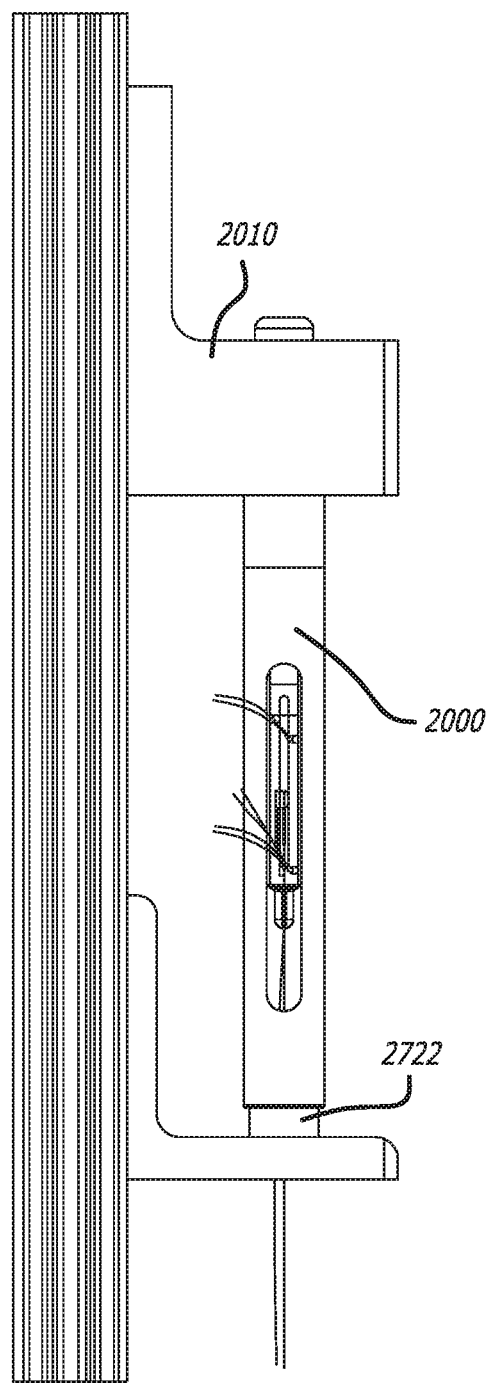
FIG. 21 shows an instrumented autoinjector mounted on a fixture in accordance with an embodiment of the invention.

According to a number of embodiments of the invention, to facilitate controlling the pen position during testing, the instrumented autoinjector 2000 may be mounted into a fixture 2010. The specific design of the fixture 2010 used to hold the instrumented autoinjector 2000 may depend upon the geometry of the autoinjector being studied. One example of a fixture 2010 is built using a number of T-slot extrusions as shown in FIG. 21. The autoinjector can be mounted in one of various positions, including but not limited to vertically with the either end up, horizontally, or at an angle.

Figure 22:
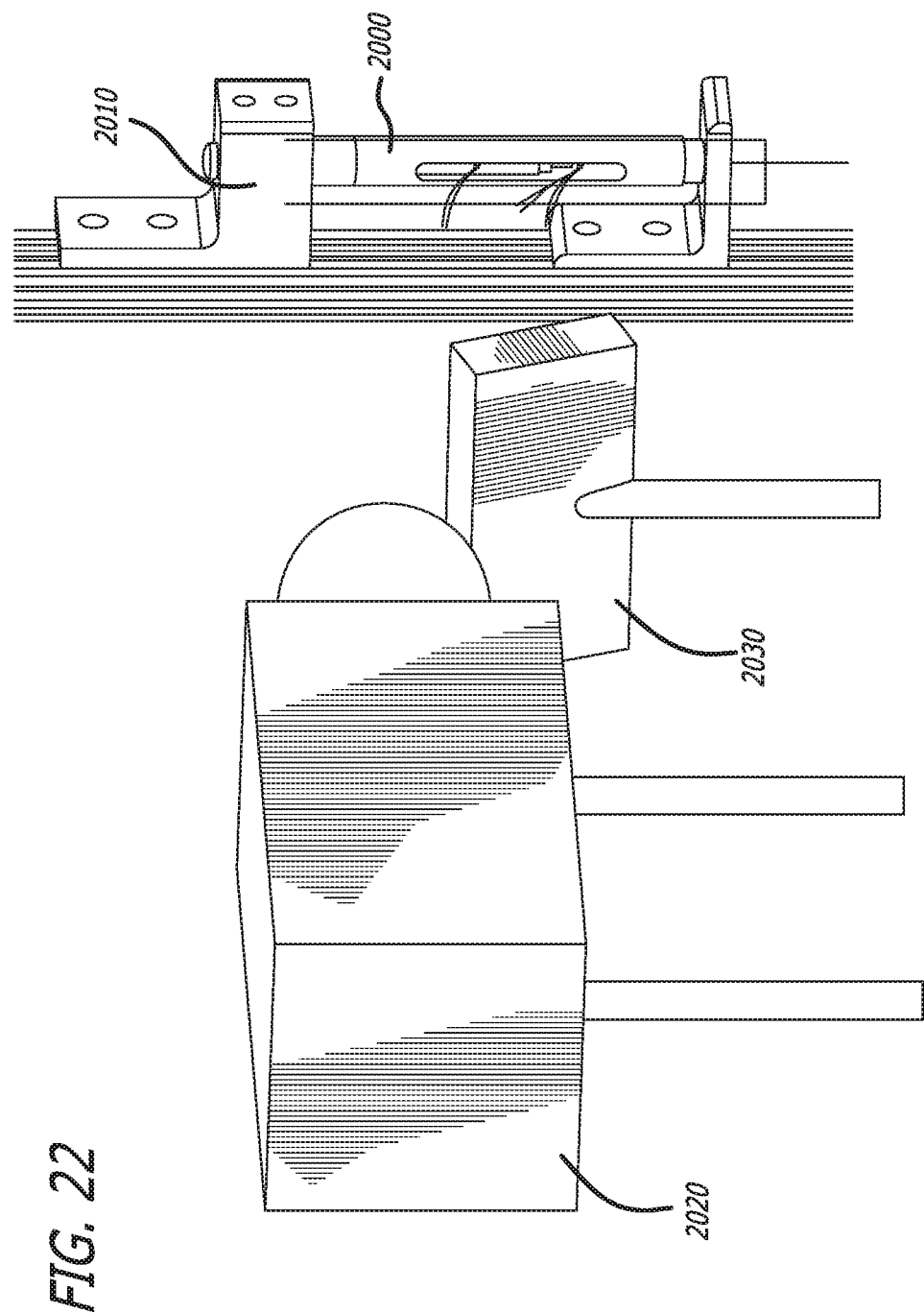
FIG. 22 shows an experimental setup for testing an instrumented autoinjector in accordance with an embodiment of the invention.

The experimental setup may be finalized according to certain embodiments of the invention. The pressure transducer 1030 and the strain gauges 1040 may be connected to signal conditioners using, for example, a soldering iron and rosin-core solder. An accelerometer can be used to trigger a data acquisition system used to perform the test, so as to cause the capture of data only when the autoinjector is activated, and may, for example, be mounted on the fixture 2010 holding the instrumented autoinjector 2000. The accelerometer may have an analog output that is provided to an A/D converter in the signal conditioning circuitry. Additionally, a high-speed camera 2020 may be mounted close to the autoinjector 2000 along with a bright light source 2030. One of various types of video cameras, including but not limited to high-speed digital cameras such as a Phantom Digital High-Speed Camera from Vision Research of Wayne, N.J., may be used for visualization during the tests. The final configuration is depicted in FIG. 22.

The mounted instrumented autoinjector 2000 may be actuated for testing in accordance with several embodiments of the invention. The camera 2020 may record the actuation of autoinjector 2000 along with movements of internal components. The pressure transducer 1030 and strain gauges 1040 may sense pressure and strain respectively, and transmit signals to the signal conditioners. The signal conditioners may manipulate the data, for example, from analog to digital format.

Once the device is actuated, it may not be recommended to reuse the same syringe a second time. Since there is often lubricant placed on the inside wall of autoinjector syringes, the first shot actuation of the device may cause a portion of the lubricant to be removed. As a result, performing more than one test with the same syringe may yield dissimilar results from one experiment to the other.

The methods of in situ measurement of forces within autoinjectors according to many embodiments of the invention as described above, may allow for unprecedented accuracy and precision in the results. Although examples of installed pressure transducers and strain gauges are discussed above and shown in the figures, it may be readily appreciated that one type of sensor could be used without another, and that the number of different types of sensors used may vary according to the requirements of a specific application in accordance with various embodiments of the invention.

While methods and systems for performing in situ strain and pressure measurements in an autoinjector are described above with respect to FIGS. 13-22, other systems and methods may be utilized as appropriate to the requirements of a specific application in accordance with various embodiments of the invention. Pressures and strains in an undamped autoinjector as measured in accordance with some embodiments of the invention are discussed further below.

Pressures and Strains in an Undamped Autoinjector

As one example of forces within an autoinjector, the pressure within the liquid contained in the syringe along with the hoop and axial strains on the outer wall of the syringe have been measured for an autoinjector similar to the device shown in FIG. 1. These in situ measurements on the original device, using instrumentation of the autoinjector according to an embodiment of the invention as discussed in the above section, can help develop a physical understanding of various mechanical events within the device, and the fluid-structure interaction between the syringe and the liquid it contains. The measurements may also provide a baseline from which to assess the effectiveness of dampers in mitigating the liquid pressure and the strains resulting from the mechanical events.

In this particular experiment, the pressure measurements were performed using a PCB 138M186 piezoelectric pressure sensor designed for underwater explosions, and the strain measurements were performed using C2A-06-015LW-120 strain gauges, in an autoinjector instrumented for force measurements according to an embodiment of the invention as described in the above section. It can be readily appreciated that various other types of sensors may be employed to perform pressure and strain measurements in an autoinjector, in accordance with various embodiments of the invention.

Figure 23:
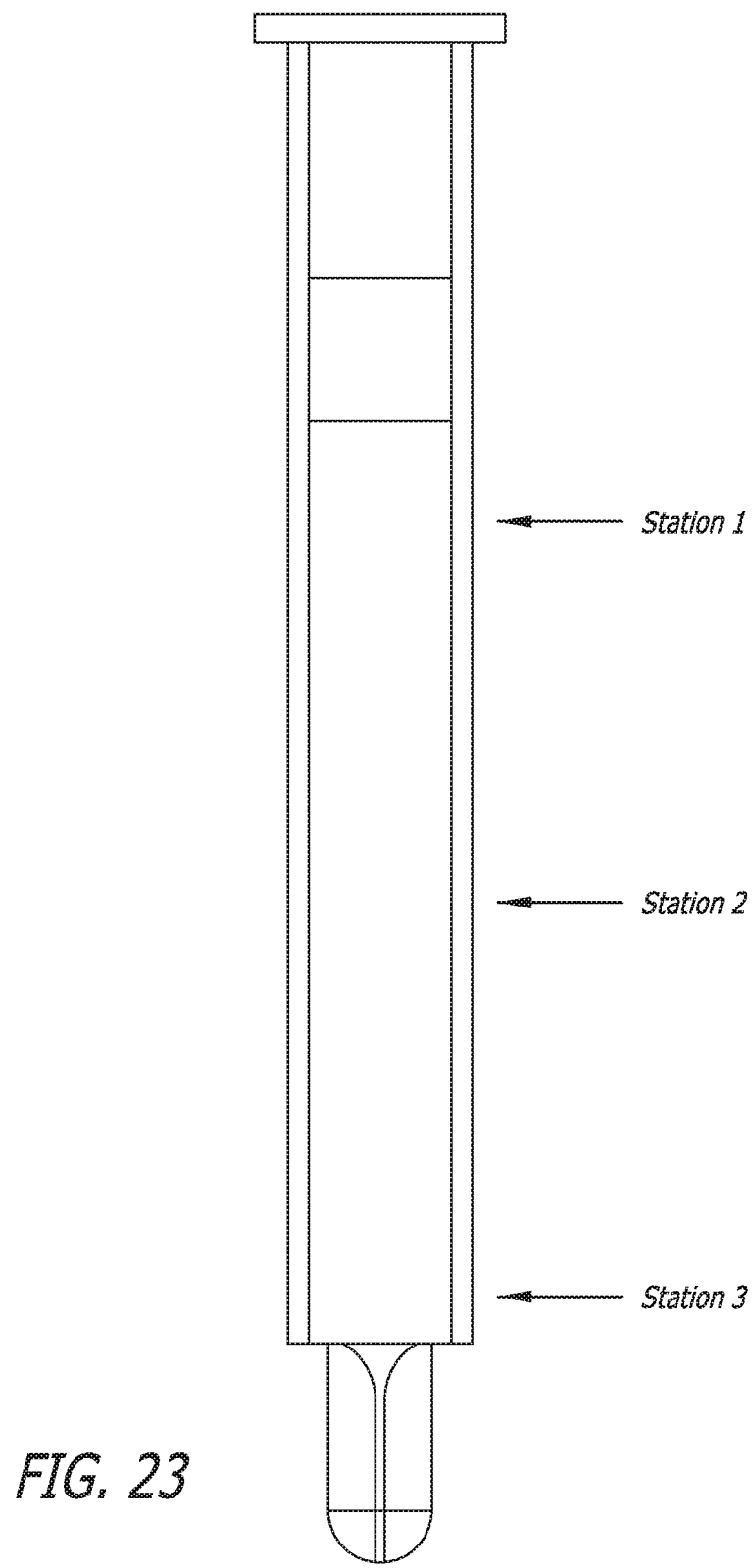
FIG. 23 shows three stations where forces can be measured in an experiment performed in accordance with an embodiment of the invention.

The pressure in the liquid contained inside the syringe was measured at three different locations as shown in FIG. 23: immediately below the stopper (station 1), halfway between the bottom end of the stopper and the converging section (station 2), and immediately above the converging section (station 3).

Figure 24:
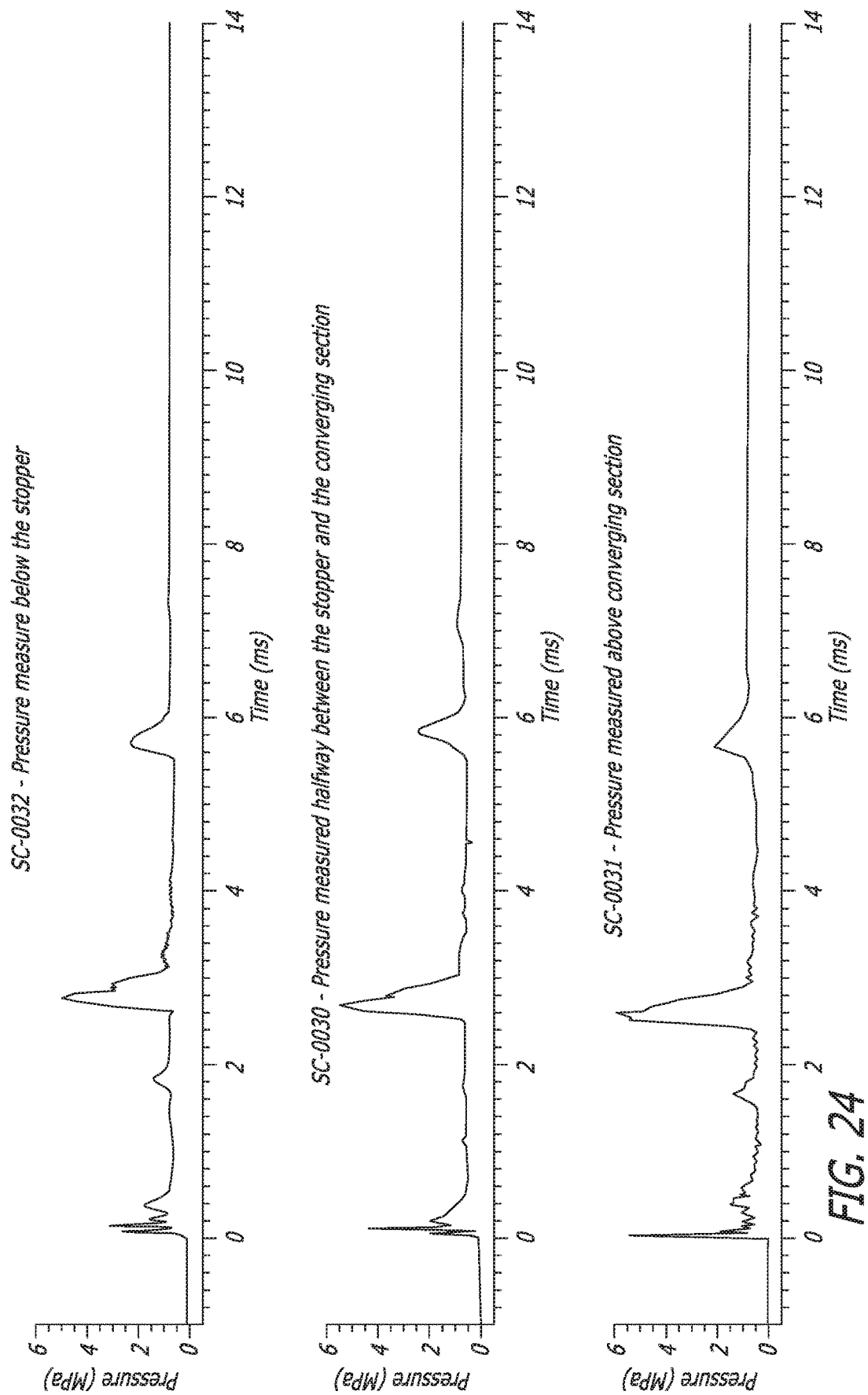
FIG. 24 shows charts illustrating pressure measurements in an experiment performed without dampers in accordance with an embodiment of the invention.

The pressure traces at the three stations are shown in FIG. 24, with each corresponding to a different test and performed using a new instrumented autoinjector, as labeled. The location of the pressure transducer for each experiment is indicated above each individual plot. The first pressure peak observed at approximately 0 ms was a result of the first event. The maximum pressure due to this event was approximately 3 to 6 MPa; the exact value depended on the location of the pressure measurement and the impact velocity of the plunger on the stopper. The second pressure peak observed approximately 2.5 ms later was due to the second event. The maximum pressure due to this event was approximately 5 to 6 MPa, and the exact value depended again on the location of the sensor and on the impact velocity.

Figure 25:
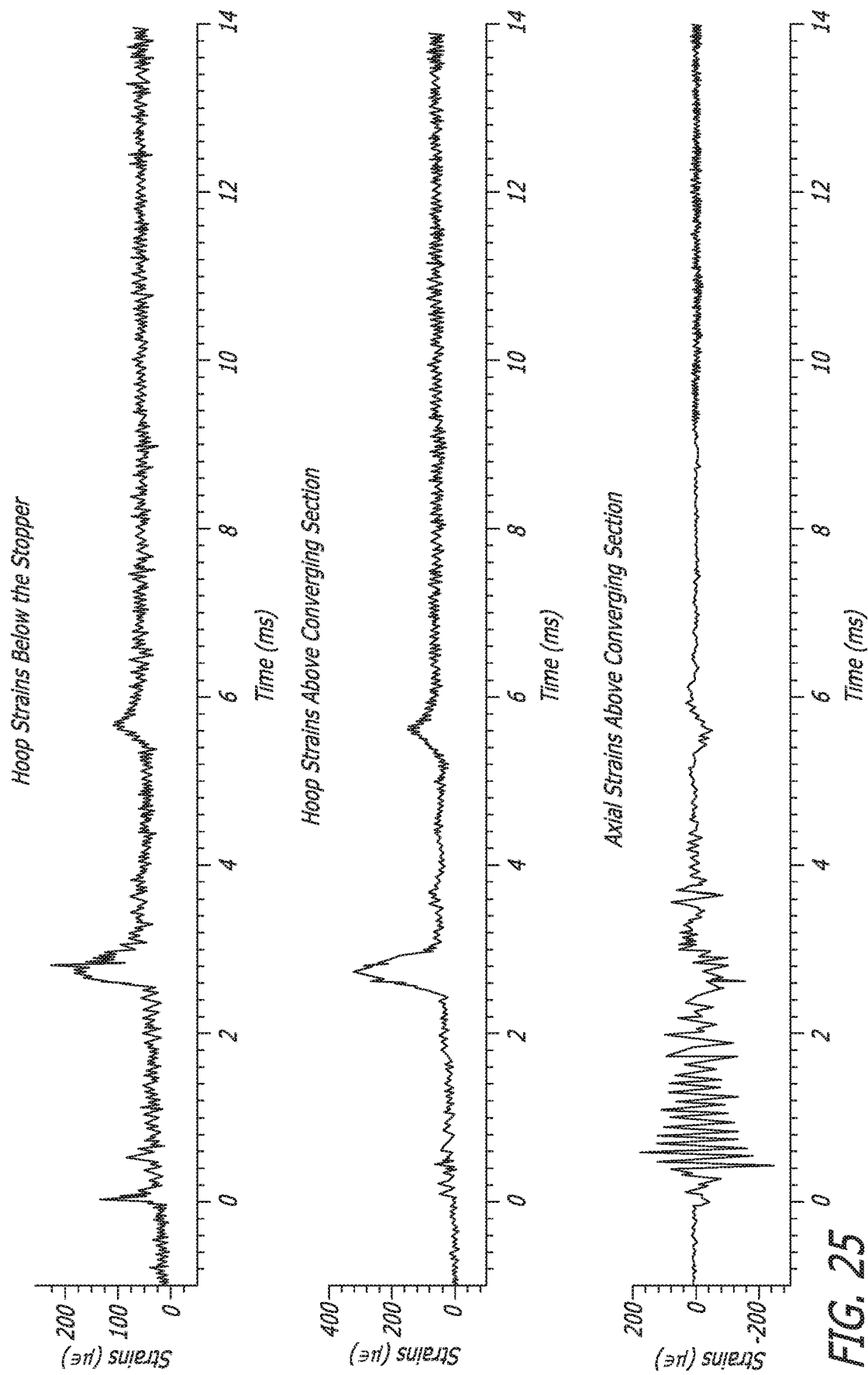
FIG. 25 shows charts illustrating strain measurements in an experiment performed without dampers in accordance with an embodiment of the invention.

In a separate test, hoop strains (aligned with the circumference of the syringe) and axial strains (aligned with the axis of the syringe) were measured on the outer wall of the syringe. The hoop strains were simultaneously measured both immediately below the stopper (station 1) and immediately above the converging section (station 3). The axial strains were only measured immediately above the converging section (station 3). The strain signals are shown in FIG. 25.

Figure 26:
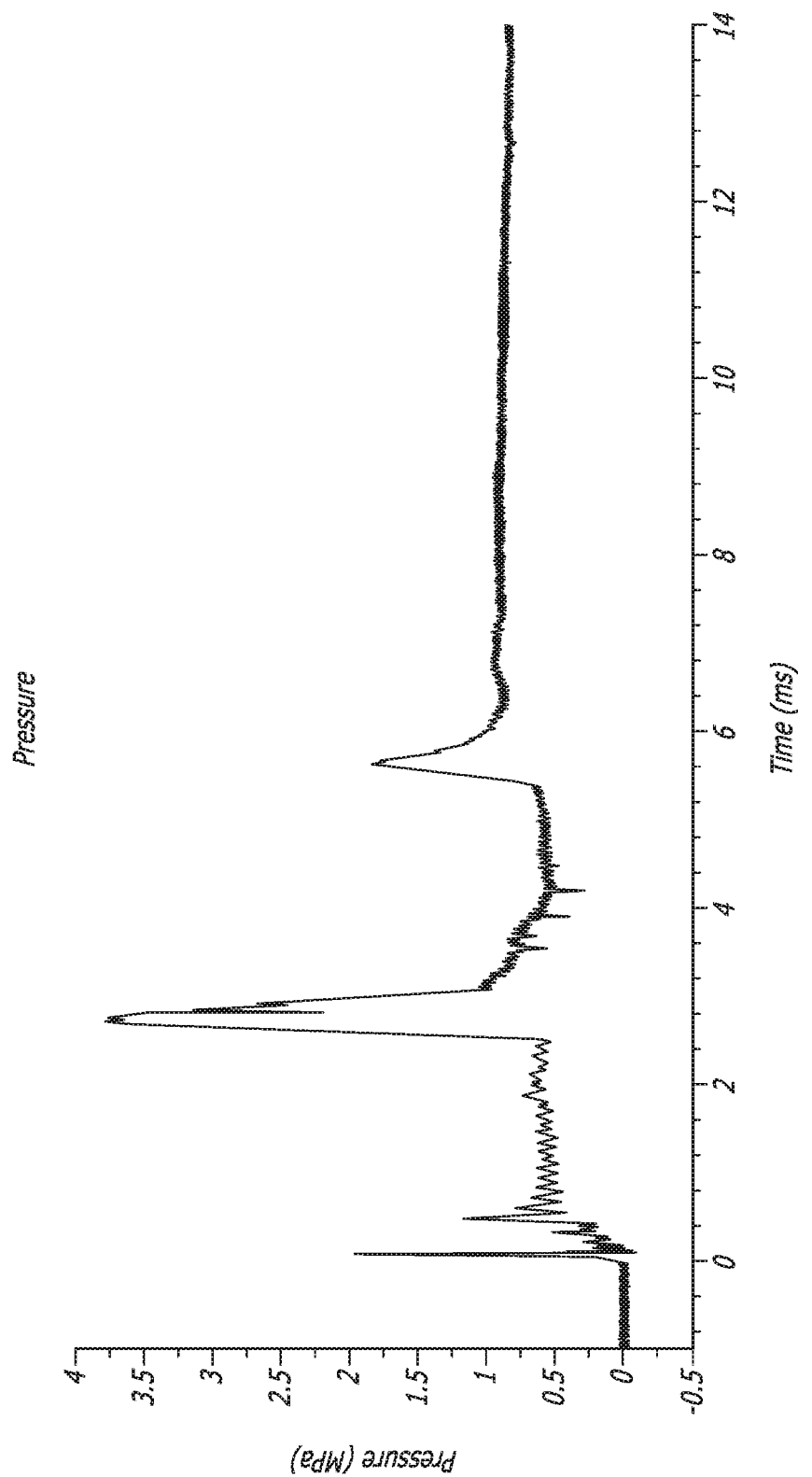
FIG. 26 is a chart illustrating pressure measurements at one station in an experiment performed without dampers in accordance with an embodiment of the invention.

The corresponding pressure in this test, measured halfway between the stopper and the converging section (station 2) is shown in FIG. 26. The spring constant for this test was approximately 500 N/m. The first pressure peak observed at approximately 0 ms is due to the first event. The maximum pressure due to this event is close to 2 MPa. The second pressure peak observed approximately 2.5 ms later is due to the second event. The maximum pressure due to this event is approximately 4 MPa, and the exact value depends again on the location of the sensor and on the impact velocity. A third event is also observed in this experiment because the syringe rebounded after the second event.

The strains related to the first event are due to the pressure wave traveling within the liquid, resulting in maximum hoop strains of approximately 125 µε and maximum axial strains of approximately 250 µε. Strains in the conical section of the syringe could potentially be larger, as the geometry of the cone may lead to focusing (i.e., amplification) of the pressure waves. The strains associated with the second event are much larger than the strains associated with the first event. Again, the net strains (hoop and axial) are due to the superposition of the strains from the axial mechanical loading of the glass as well as the internal pressure waves in the liquid. The maximum hoop strains due to this second event are approximately 320 µε and the maximum axial strains are approximately 175 µε

It is possible to estimate the order of magnitude of the mechanical stresses in the glass from σ~Eε=65 GPa×320 µε=21 MPa. From this it may be concluded that the stresses in the glass could be sufficiently large for failure to occur.

While pressures and strains measured in an experiment using an undamped autoinjector are described above with respect to FIGS. 23-26, other experiments may be conducted as appropriate to the requirements of a specific application in accordance with various embodiments of the invention. Dampers for autoinjectors in accordance with a number of embodiments of the invention are discussed further below.

Dampers for Autoinjectors

In an autoinjector, the injection and needle motion is typically controlled primarily by the quasi-static spring force, rather than by peak pressures or peak forces due to transients associated with mechanical events that occur during operation of the device. Thus, the large peak pressures and strains that occur, such as those reported in the previous section for the undamped autoinjector, are therefore unnecessary for device performance and can be damped without affecting the injection function of the device. According to many embodiments of the invention, proper damping of first and second events may reduce the probability of mechanical failure of the syringe due to peak stresses in the glass exceeding a failure threshold. This may be achieved by adding dampers within the device to absorb a substantial fraction of the mechanical energy, and therefore reduce significantly the impact velocities, acceleration, and/or deceleration of the components.

According to a number of embodiments of the invention, the dampers are configured so as not to modify the behavior of the device in such a way that it does not serve its main purpose for injection effectively anymore. Thus, in certain embodiments of the invention, the dampers may be configured to meet these five conditions: 1) they effectively mitigate the first and second events; 2) there is still enough force for the needle to penetrate the skin; 3) there is sufficient force to inject the drug solution liquid through the needle with an adequate flow rate; 4) the time needed to fully extrude the liquid should not be significantly increased; and 5) the penetration length of the needle should not be significantly decreased.

The first condition may be met by using a material for the damper which exhibits a hysteretic response, or the state of which is dependent on its history (e.g., memory foam). The second condition may be achieved by using a material which can be compressed over a short period of time by the actuation mechanism of the autoinjector, but will take a much longer time to relax and return to its initial configuration when the forces are removed (i.e., material with low resilience), or materials which do not return to their original shape. The third condition may be met by using a damping material that does not significantly affect the quasi-static spring force, and/or a low-resilience material. The fourth and fifth conditions may be met by using a material with a relatively large compliance such that the dampers can be greatly compressed, and the travel distance of the syringe and the needle is effectively unchanged as compared to the case without dampers.

Examples of materials that may be used include, but are not limited to, low-resilience polyurethane foam, also known as LRPU or viscoelastic polyurethane foam, viscoelastic urethane polymer, neoprene, various other types of foam, low-density rubber, and/or crushable structures including but not limited to honeycomb structures designed to absorb energy. In certain embodiments of the invention, a frictional damper may be used to create sliding friction between the body of the autoinjector and the moving components. In other embodiments of the invention, a fluidic damper may be employed, using fluid viscosity to damp mechanical motion. In addition, any materials that are hysteretic, low-resilience, and/or high loss modulus may be desirable for damping. Further, any one or a combination of various materials that can effectively damp forces created by moving components inside an autoinjector may be used, and are not limited to any specific materials named as examples herein.

Figure 27:
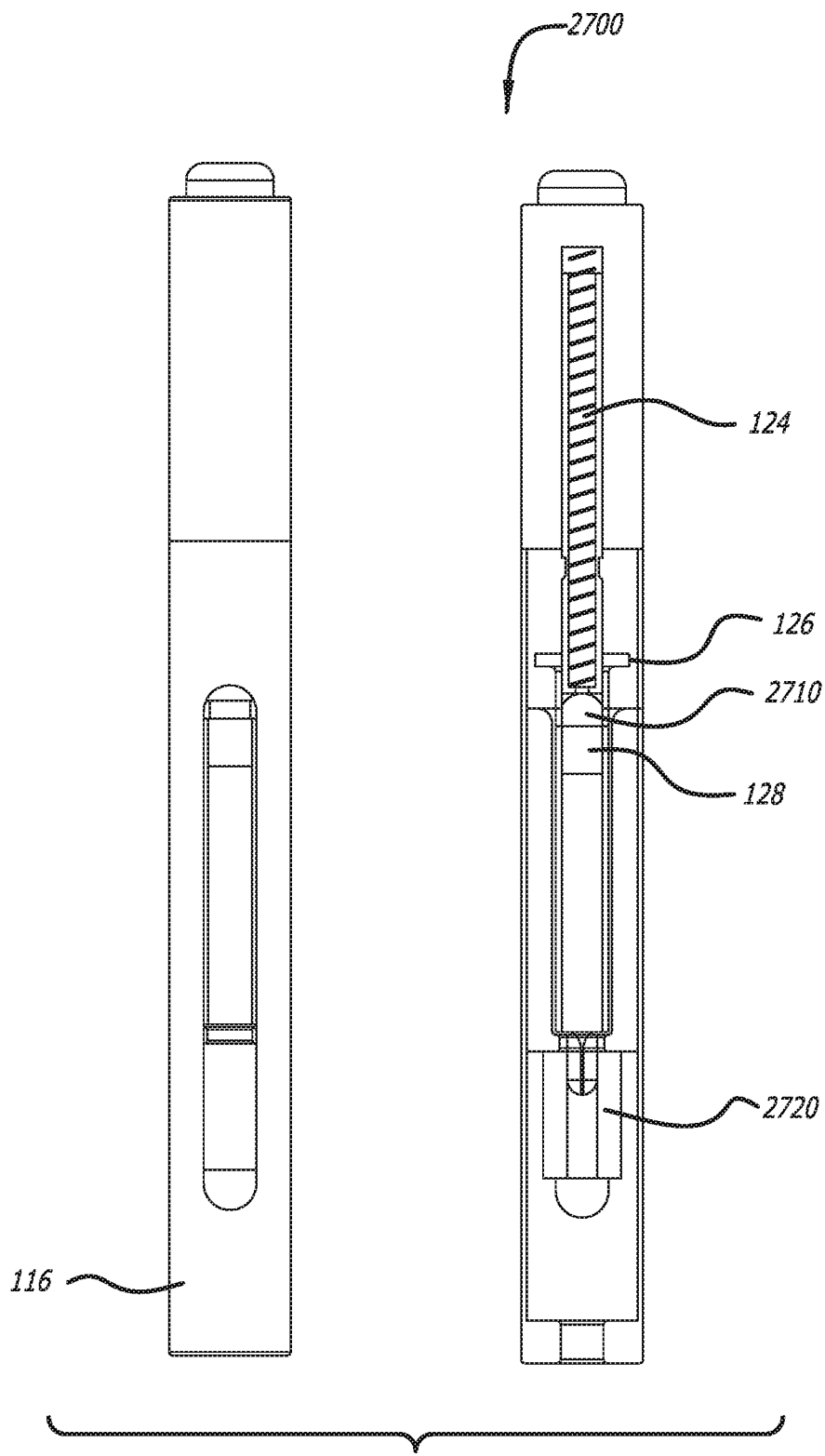
FIG. 27 is a schematic diagram showing a spring-actuated autoinjector with dampers.

Referring to FIG. 27 showing a damping system 2700 according to an embodiment of the invention, a top damper 2710 is formed of a material which exhibits the properties discussed above, and introduced between the bottom end of plunger 124 and the top end of stopper 128. Top damper 2710 may effectively damp the first event, such that the peak magnitude of the pressure wave will be reduced, thus mitigating the hoop and axial stresses in the syringe 126. If a bottom damper 2720 made of, for example, the same material is also introduced at the bottom end of the syringe 126, or between the syringe 126 and the shell 116, the peak stresses in the syringe due to the second event may also be mitigated. The exact locations of the top and bottom dampers may vary with the geometry and properties of a particular autoinjector, and such adjustments are contemplated within the scope of this invention. In addition, one or more of the dampers 2710 and 2720 may potentially be built into the plunger 124, stopper 128, syringe 126, shell 116, or one or more other parts of an autoinjector.

In many autoinjection devices, the translational motion of the syringe can be controlled and/or limited using a flange and/or shoulder of the syringe, and/or a stopper. Sometimes the forces may be applied to a syringe carrier into which the syringe is mounted. A damper could be used between the part(s) of the syringe or carrier where a force is applied to accelerate or decelerate the syringe, and the component contacting the syringe to apply this force. Thus, contact points between the syringe (or its carrier) and the driving mechanism, as well as contact points between the syringe (or its carrier) and a feature limiting the motion of the syringe, are good candidates for damping to be applied.

In many autoinjectors, there is a stopper sealing the syringe. The geometry of the stopper can vary from one device to the other. When a stopper is used, it is often linked to a driving mechanism responsible for moving this stopper in order to perform the injection of the liquid drug and, in some cases, to initiate the translational motion of the syringe. The contact point between this driving mechanism and the stopper may be a good candidate for damping to be applied.

The dampers 2710 and 2720 may be formed of one or more of various types of materials that meet the conditions for both effective damping and function of the device, as outline above. One example of such a material is low-resilience polyurethane foam, also known as LRPU or viscoelastic polyurethane foam. The specific foam used in the experiments reported in the section below was Pura-Fit 6800 from Moldex of Culver City, Calif. The Pura-Fit 6800 is an ear plug made out of a high-density viscoelastic polyurethane foam, with an approximate density of 0.23 g/cm3 or 14 pounds per cubic foot. In addition, hydraulic dampers may potentially be used. Any one or combination of other materials and mechanisms may be used and/or coordinated together to damp forces in autoinjectors, in accordance with various embodiments of the invention. Other mechanical elements, such as but not limited to screws, can be used to deliver the drug and transport the needle while also minimizing unwanted acceleration or impact forces.

The dampers 2710 and 2720 may be formed into various shapes as appropriate to meet the conditions described above. They may be disk-shaped, cylindrical and/or formed to fit snugly in the spaces where they are to be positioned. As an example and not by way of limitation, a top damper used in an autoinjector similar to the device shown in FIG. 1 may be disk-shaped with a diameter just slightly larger than the inner diameter of the syringe. The height of the disk may be approximately the initial distance between the plunger and the stopper. Using an uncompressed foam disk of such dimensions would fill the gap between the plunger and the stopper of an autoinjector similar to that shown in FIG. 1, prior to firing of the autoinjector. Similarly, as an example and not by way of limitation, a bottom damper used in an autoinjector similar to the device shown in FIG. 1 may be cylindrically shaped to be inserted between the syringe and the shell. A hole centered on the axis of symmetry of the cylinder may be made to accommodate the tip of the syringe and the needle.

While examples of dampers are provided with respect to autoinjector similar to the device shown in FIG. 1, it may be readily appreciated that the damping system 2700 is not limited to any particular autoinjector, and may be implemented according to a number of embodiments of the invention as described above. Further, the exact mechanisms of damping or the details of the autoinjector may vary within the scope of the invention. Modifications may be implemented to vary the density, geometry, and/or positioning of the damping foam, so as to improve results.

While dampers for autoinjectors are described above with respect to FIG. 27, other devices may be utilized as appropriate to the requirements of a specific application in accordance with various embodiments of the invention. Pressures and strains in a damped autoinjector as measured in accordance with some embodiments of the invention are discussed further below.

Pressures and Strains in a Damped Autoinjector

Several experiments were performed to assess the effectiveness of the damping system 2700 as implemented according to some embodiments of the invention in an instrumented version of an autoinjector similar to the device shown in FIG. 1. Although only one such experiment is discussed herein, repeated tests have demonstrated that the results are reproducible and exceedable, with damping of the peak pressure and the peak strains by as much as 75% being observed. Using in situ measurement techniques according to some embodiments of the invention as discussed above, the dampers were shown to significantly reduce peak pressures and strains in the syringe. Although the peak pressures and strains were substantially reduced, the injection function of the device was not significantly affected by the presence of dampers.

During this particular testing with a damped version of an autoinjector similar to the device shown in FIG. 1, the bottom end of the autoinjector was rested on a support member 2722 (shown in FIG. 21) made of nylon. The support member 2722 comprised an inner hole, the diameter of which was approximately 5 mm. The support member 2722 effectively blocked a portion of the opening at the bottom of the device, so as to support the bottom damper 2720 from below, prevent excessive downward extrusion of the bottom damper 2720, and provide sufficient damping force.

Figure 28:
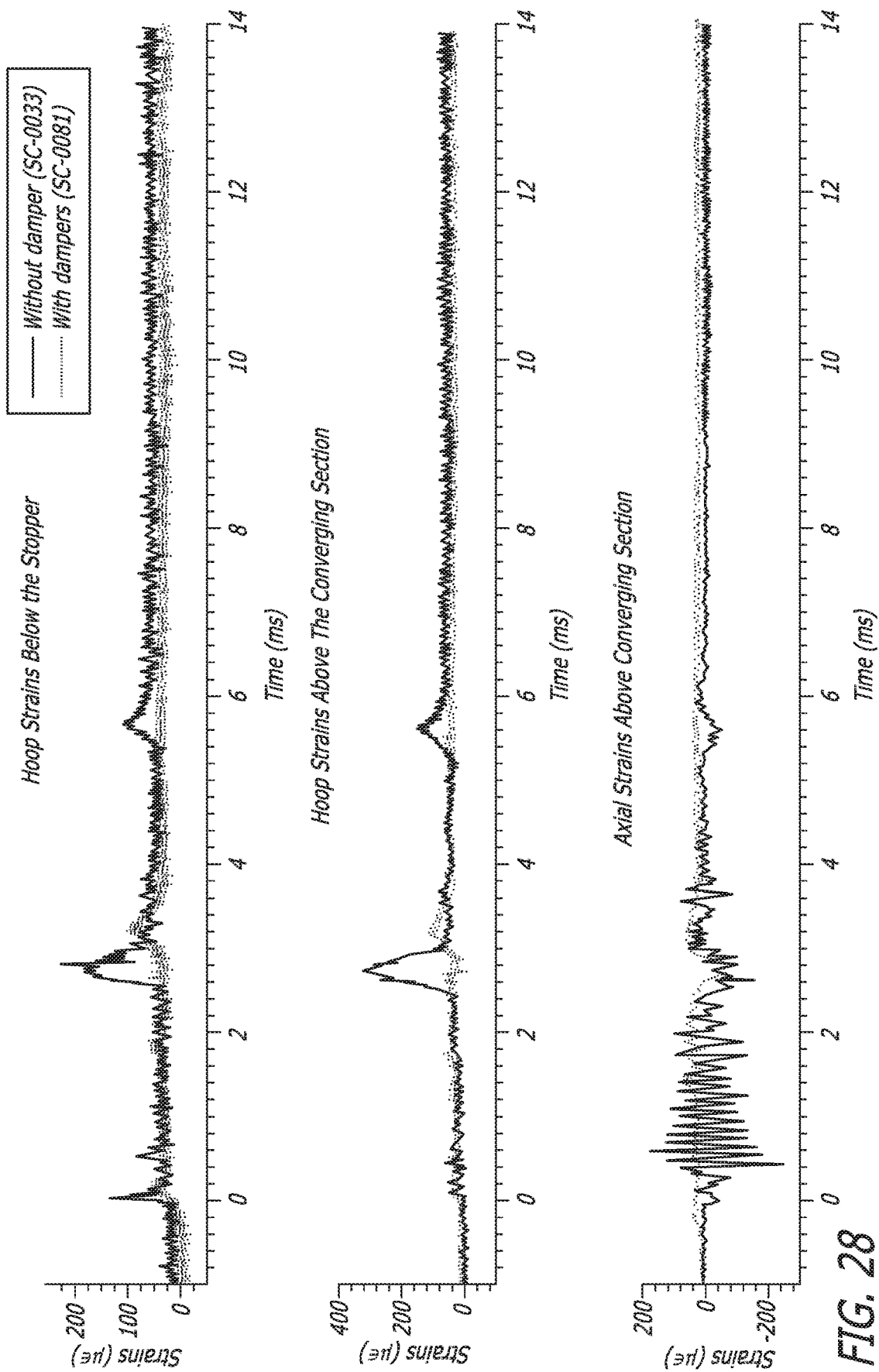
FIG. 28 shows charts illustrating strain measurements in an experiment performed with dampers in accordance with an embodiment of the invention.
Figure 29:
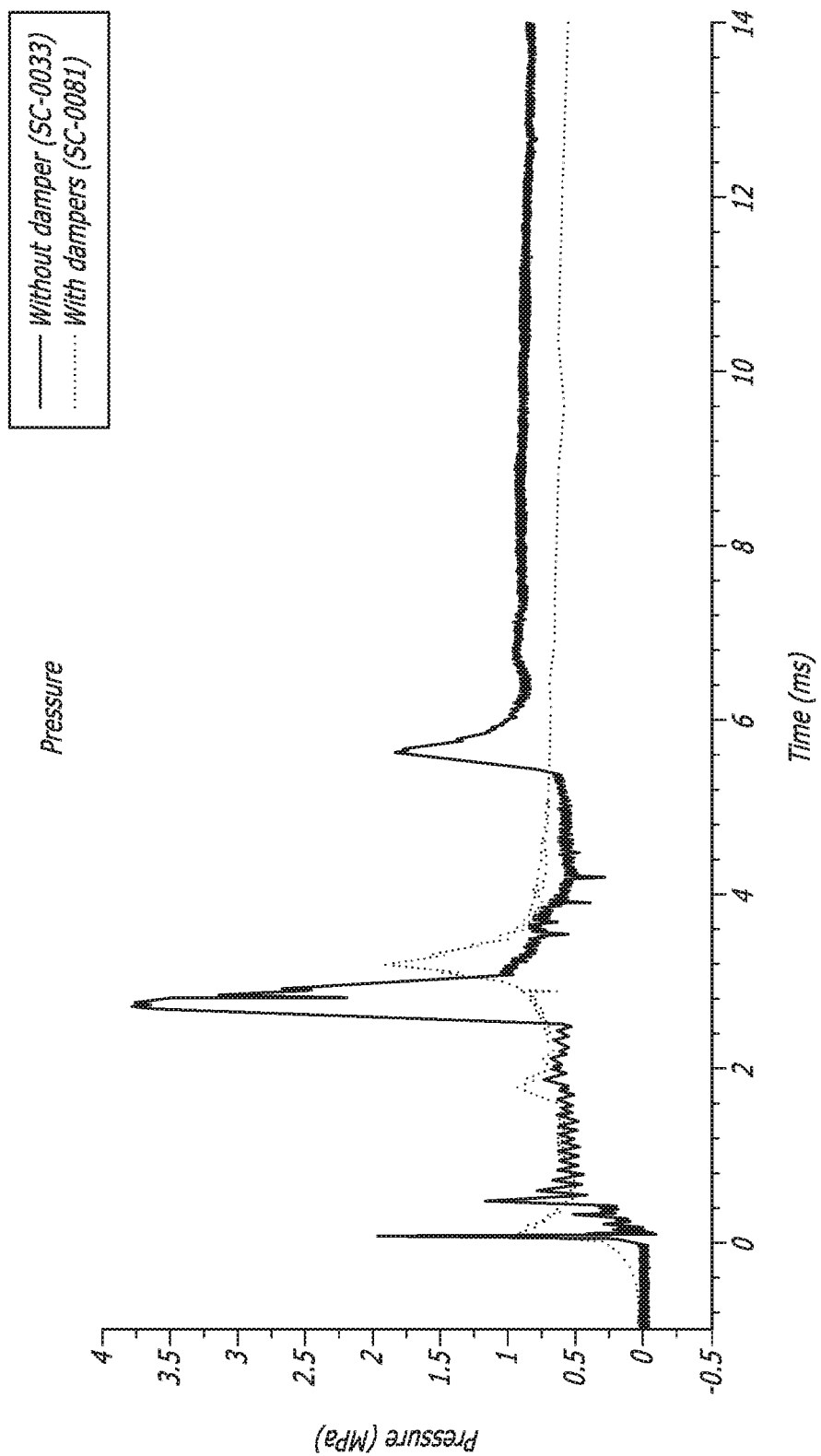
FIG. 29 is a chart illustrating pressure measurements at one station in an experiment performed with dampers in accordance with an embodiment of the invention.

For a test measuring forces within an actuated autoinjector including a damping system according to some embodiments of the invention described previously, measurements were collected at the three stations shown in FIG. 23. The pressure was measured at station 2, the hoop strains were measured at station 1 and 3, and the axial strains were measured at station 3. The spring constant was approximately 545 N/m. The experimental results for this test are shown in FIGS. 28 and 29. The results for the previous test without dampers as shown in FIGS. 25 and 26, are also included in FIGS. 28 and 29 to highlight the effect of the dampers on the strains and internal pressure. The spring constant for the test without dampers was 500 N/m (about 10% lower than for the test with dampers).

As can be seen in the strain signals of FIG. 28, the dampers significantly mitigate the first and second events. In this experiment, the first event was hardly noticeable, and the maximum strains due to the second event were reduced. The maximum hoop strains were approximately 116 $\mu\varepsilon$, or reduced by as much as 64% compared to the undamped case. The maximum axial strains were approximately 78 $\mu\varepsilon$, or reduced by as much as 69% compared to the undamped case.

Examining the pressure signal shown in FIG. 29, both the first and second events were visible. The magnitude of the pressure, however, remained below 2.0 MPa. As a result, the peak pressure was reduced by as much as 50%. Another difference between the damped and undamped cases is in the final pressure measured at t=14 ms. In the damped case, this final pressure is approximately 0.6 MPa. In the undamped case, the final pressure is approximately 0.85 MPa. As an added benefit of damping, the third event has been successfully eliminated. This can be observed from the pressure and strain signals.

Using high-speed imaging, it was also verified that the presence of the dampers did not significantly increase the time needed to extrude the liquid from the syringe despite the lower residual pressure. In fact, no significant difference was observed in the injection time when the syringe contained water. An increase of no more than 10% in the extrusion time was observed when the syringe contained a viscous silicone oil (viscosity of 5 cSt). The observed variations in extrusion time are within the test-to-test variations found in the limited testing carried so far. Using high-speed imaging, it was also verified that the dampers did not reduce the travel distance (i.e., the penetration length) of the needle.

According to certain embodiments of the invention, by damping the mechanical events within autoinjectors, autoinjectors may be powered by stiffer power packs that enable the use of more viscous drugs and/or smaller diameter needles. The user experience may also be improved by the damping of the events, even for low-viscosity drugs, as the dampers may reduce considerably the sensation of abrupt motion of the device. Significantly, the modification of damping may drastically reduce failures of glass syringes due to event-generated forces.

Although a damped version of an auto-injector similar to the device shown in FIG. 1 was used to assess the validity of the damping method suggested, the idea can be extended to other designs of autoinjectors. It can be readily appreciated that the materials, placement and geometry of the dampers should be adequately adapted for each autoinjector to optimally mitigate the mechanical events. Further, while pressures and strains measured in an experiment using a damped autoinjector are described above with respect to FIGS. 21, 23, 25-26, and 28-29, other experiments may be conducted as appropriate to the requirements of a specific application in accordance with various embodiments of the invention.

CONCLUSION

Although the present invention has been described in certain specific aspects, many additional modifications and variations would be apparent to those skilled in the art. It is therefore to be understood that the present invention can be practiced otherwise than specifically described without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A method for measuring pressure and strain in an instrumented autoinjector, comprising:
    creating an autoinjector shell, the autoinjector shell being elongated and hollow for housing autoinjector components, including a syringe and a syringe carrier;
    installing a pressure transducer inside the syringe;
    filling the syringe with fluid;
    installing at least one strain gauge on an outer surface of the syringe;
    assembling an instrumented autoinjector by:
        mounting the syringe with the pressure transducer, the fluid, and the at least one strain gauge into the syringe carrier; and
        mounting the syringe carrier into the autoinjector shell;
    activating the instrumented autoinjector;
    measuring liquid pressure in the syringe by recording data transmitted from the pressure transducer; and
    measuring hoop and axial strains on the outer surface of the syringe by recording data transmitted from the at least one strain gauge.

2. The method of claim 1, further comprising:
    removing a needle from the syringe;
    wherein installing the pressure transducer includes:
        inserting at least one magnet wire into the syringe; and
        connecting a first end of the at least one magnet wire to at least one leadwire of the pressure transducer, wherein a second end of the at least one magnet wire extends out of the syringe through a needle opening of the syringe.

3. The method of claim 1, wherein the fluid includes deionized water.

4. The method of claim 1, wherein installing the at least one strain gauge includes:
    bonding a portion of at least one leadwire of the at least one strain gauge to the outer surface of the syringe.

5. The method of claim 1, further comprising:
    forming an opening in the syringe carrier;
    wherein:
    the at least one strain gauge includes at least one leadwire;
    mounting the syringe into the syringe carrier includes:
        directing the at least one leadwire of the at least one strain gauge through the opening formed in the syringe carrier; and
    mounting the syringe carrier into the autoinjector shell includes:
        directing the at least one leadwire of the at least one strain gauge through an opening of the autoinjector shell.

6. The method of claim 1, wherein assembling the instrumented autoinjector is further performed by:
    mounting a power pack to the autoinjector shell.

7. The method of claim 1, further comprising:
    connecting at least one leadwire of the pressure transducer and at least one leadwire of the at least one strain gauge to signal conditioners.

8. The method of claim 1, further comprising:
    mounting the instrumented autoinjector onto a fixture.

9. The method of claim 1, further comprising:
    positioning a high-speed camera external to and in proximity to the instrumented autoinjector such that the high-speed camera is capable of capturing movement of components within the instrumented autoinjector upon activation of the instrumented autoinjector.

10. The method of claim 1, wherein dimensions of the autoinjector shell simulate dimensions of a shell of an original autoinjector, and the autoinjector components include components of the original autoinjector, such that the pressure and strain measured in the instrumented autoinjector simulate pressure and strain in the original autoinjector when activated.

11. The method of claim 1, wherein at least one portion of the autoinjector shell is formed to be clear.

* * * * *